United States Patent [19]

Doria et al.

[11] Patent Number: 4,853,405

[45] Date of Patent: Aug. 1, 1989

[54] CONDENSED PYRAZOLE DERIVATIVES, PHARMACEUTICAL COMPOSITIONS AND USE

[75] Inventors: Gianfederico Doria, Milan; Anna M. Isetta, Rho; Mario Ferrari; Domenico Trizio, both of Milan, all of Italy

[73] Assignee: Farmitalia Carlo Erba S.r.l., Milan, Italy

[21] Appl. No.: 144,330

[22] Filed: Jan. 15, 1988

[30] Foreign Application Priority Data

Jan. 21, 1987 [GB] United Kingdom ................. 8701238
Sep. 18, 1987 [GB] United Kingdom ................. 8721972
Oct. 27, 1987 [GB] United Kingdom ................. 8725085

[51] Int. Cl.[4] .................... A61K 31/415; A61K 31/44; C07D 231/54; C07D 491/06

[52] U.S. Cl. .................................... 514/406; 514/333; 514/338; 546/256; 546/271; 548/369

[58] Field of Search ....................... 546/279, 271, 256; 548/369; 514/341, 333, 406, 338

[56] References Cited

U.S. PATENT DOCUMENTS 3,940,418 2/1976 Hamilton ........................... 548/371

*Primary Examiner*—Robert W. Ramsuer
*Attorney, Agent, or Firm*—Armstrong, Nikaido, Marmelstein & Kubovcik

[57] ABSTRACT

The invention relates to compounds having the general formula (I)

(I)

and the pharmaceutically acceptable salts thereof, which possess immunomodulating activity and are useful e.g. in the treatment of neoplastic diseases and acute and chronic infections of both bacterial and viral origin in mammals.

7 Claims, No Drawings

CONDENSED PYRAZOLE DERIVATIVES, PHARMACEUTICAL COMPOSITIONS AND USE

The present invention relates to new condensed pyrazole derivatives, to a process for their preparation and pharmaceutical compositions containing them.

The compounds of the invention have the general formula (I)

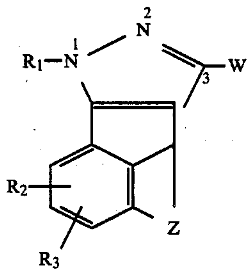

wherein

Z represents a $C_2$–$C_6$ alkylene chain or a —CH=CH—CH= group or an —E—$CHR_4$—$(CH_2)_p$— group, in which p is zero, 1 or 2;

E represents an oxygen atom or a $>S(O)_q$ group, wherein q is zero, 1 or 2; and $R_4$ is hydrogen or $C_1$–$C_3$alkyl;

$R_1$ represents $C_1$–$C_6$ alkyl, benzyl, pyridyl or phenyl, the phenyl being unsubstituted or substituted by one or two substituents chosen independently from halogen, trifluoromethyl, $C_1$–$C_6$ alkyl, $C_1$–$C_6$ alkoxy, nitro, amino, formylamino and $C_2$–$C_8$ alkanoylamino;

each of $R_2$ and $R_3$ is independently:

(a) hydrogen, halogen or $C_1$–$C_6$ alkyl;

(b) hydroxy, $C_1$–$C_6$ alkoxy or $C_3$–$C_4$ alkenyloxy; or (c) nitro, amino, formylamino or $C_2$–$C_8$ alkanoylamino; and W represents:

(a') a

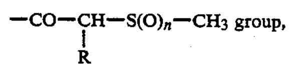

wherein n is 1 or 2 and R represents hydrogen or $C_1$–$C_6$ alkyl; or (b') a

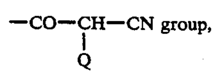

wherein Q represents hydrogen, carboxy, $CONH_2$, $C_2$–$C_7$ alkoxycarbonyl or a

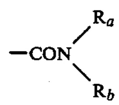

or a

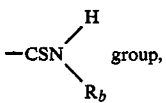

wherein $R_a$ represents hydrogen or $C_1$–$C_{20}$ alkyl and $R_b$ represents $C_1$–$C_{20}$ alkyl or a —$(CH_2)_m$—$R_5$ group, wherein m is zero, 1 or 2 and $R_5$ is:

(a'') $C_5$–$C_8$ cycloalkyl;

(b'') pyridyl unsubstituted or substituted by one or two substituents chosen independently from halogen, $C_1$–$C_6$ alkyl and $C_1$–$C_6$ alkoxy; or (c'') phenyl unsubstituted or substituted by one or two substituents independently chosen from halogen, $CF_3$, $C_1$–$C_6$ alkyl, $C_1$–$C_6$ alkoxy, amino, nitro, formylamino, $C_2$–$C_8$ alkanoylamino, di($C_1$–$C_6$ alkyl)amino, hydroxy, formyloxy and $C_2$–$C_8$ alkanoyloxy.

The present invention includes within its scope the pharmaceutically acceptable salts, and also all the possible isomers, stereoisomers and optical isomers and their mixtures, and the metabolites and the metabolic precursors or bioprecursors of the compounds of formula (I).

It has to be noticed that when in the compounds of formula (I) W is a

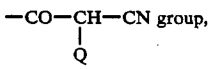

as defined above under (b'), it may be represented also by a tantomeric structure, namely the enol structure of formula (c')

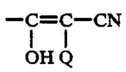

(c')

wherein

Q is as defined above.

The compounds of formula (I), wherein W is represented by the enol structure (c'), fall within the scope of the present invention too and are herein described as compounds of formula (I), wherein W is a

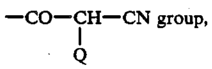

as defined under (b').

It is clear that, when in the compounds of the invention Z represents an —E—$CHR_4$—$(CH_2)_p$ group, wherein p, E and $R_4$ are as defined above, the heteroatom E is directly linked to the condensed phenyl ring in the molecule.

The alkyl, alkylene, alkanoyloxy, alkoxy, alkoxycarbonyl and alkanoylamino groups may be branched or straight chain groups.

A $C_1$–$C_{20}$ alkyl group is preferably a $C_1$–$C_6$ alkyl group.

A $C_1$–$C_6$ alkyl group is, e.g., methyl, ethyl, propyl, isopropyl, butyl or tert.butyl, more preferably methyl, ethyl or tert.butyl. A $C_1$–$C_3$ alkyl group is preferably methyl, ethyl or propyl, in particular methyl.

A $C_3$–$C_4$ alkenyloxy group is preferably allyloxy.

A $C_1$–$C_6$ alkoxy group is, e.g., methoxy, ethoxy, propoxy, isopropoxy, butoxy or tert.butoxy, preferably it is methoxy, ethoxy or propoxy.

A $C_5$–$C_8$ cycloalkyl group is preferably cyclopentyl or cyclohexyl.

A $C_2$–$C_8$ alkanoyloxy group is preferably a $C_2$–$C_5$ alkanoyloxy group, in particular acetoxy or propionyloxy.

A $C_2$–$C_6$ alkylene chain is preferably a $C_2$–$C_4$ alkylene chain, in particular —$CH_2$—$CH_2$—, —$CH_2$—$CH_2$—$CH_2$— and —$CH(CH_3)$—$CH_2$—$CH_2$—.

A $C_2$–$C_7$ alkoxycarbonyl group is preferably a $C_2$–$C_5$ alkoxycarbonyl group, in particular a $C_2$–$C_3$ one.

A $C_2$–$C_8$ alkanoylamino group is preferably a $C_2$–$C_6$ alkanoylamino group, in particular acetylamino or propionylamino.

Examples of pharmaceutically acceptable salts are either those with inorganic bases, such as sodium, potassium, calcium and aluminium hydroxides, or with organic bases, such as lysine, triethylamine, triethanolamine, dibenzylamine, methylbenzylamine, di-(2-ethylhexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic, e.g. hydrochloric, hydrobromic and sulphuric acids and with organic acids, e.g. citric, tartaric, maleic, malic, fumaric, methanesulphonic and ethanesulphonic acids. Preferred salts of the compounds of formula (I) are the sodium and the potassium salts thereof.

As stated above, the present invention also includes within its scope pharmaceutically acceptable bioprecursors (otherwise known as pro-drugs) of the compounds of formula (I), i.e. compounds which have a different formula than formula (I) above but which nevertheless upon administration to a human being are converted directly or indirectly in vivo into a compound of formula (I).

Preferred compounds of the invention are those of formula (I) wherein:

Z represents a $C_2$–$C_4$ alkylene chain or a —CH=CH—CH= group or an —E—$CHR_4$—$(CH_2)_p$— group, in which p is zero, 1 or 2;

E represents an oxygen atom or a $>S(O)_q$ group, wherein q is zero, 1 or 2; and $R_4$ is hydrogen or $C_1$–$C_3$ alkyl;

$R_1$ represents $C_1$–$C_4$ alkyl or phenyl, the phenyl being unsubstituted or substituted by one or two substituents chosen independently from amino, halogen, trifluoromethyl, $C_1$–$C_4$ alkyl, $C_1$–$C_4$ alkoxy and nitro;

each of $R_2$ and $R_3$ is independently hydrogen, halogen, $C_1$–$C_4$ alkyl or $C_1$–$C_4$ alkoxy;

W represents: a

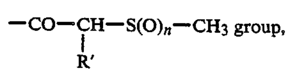

wherein n is 1 or 2 and R' represents hydrogen or $C_1$–$C_4$ alkyl; or a

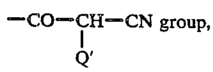

wherein Q' represents hydrogen, —$CONH_2$, $C_2$–$C_5$ alkoxycarbonyl or a —$CONR'_aR'_b$ or —$CSNHR'_b$ group, wherein $R'_a$ is hydrogen or $C_1$–$C_6$ alkyl and $R'_b$ is $C_1$–$C_6$ alkyl or a —$(CH_2)_{m'}$—$R'_5$ group wherein m' is 0 or 1 and $R'_5$ is $C_5$–$C_8$ cycloalkyl, unsubstituted pyridyl or phenyl unsubstituted or substituted by one or two substituents chosen independently from halogen, $CF_3$, $C_1$–$C_4$ alkyl, $C_1$–$C_4$ alkoxy, nitro and amino; and the pharmaceutically acceptable salts thereof.

More preferred compounds of the invention are those of formula (I) wherein:

Z represents a $C_3$–$C_4$ alkylene chain or a —CH=CH—CH= group or an E'—$CHR'_4$—$CH_2$— group, in which E' represents an oxygen or a sulphur atom and $R'_4$ is hydrogen or $C_1$–$C_3$ alkyl;

$R_1$ represents $C_1$–$C_2$ alkyl or phenyl, the phenyl being unsubstituted or substituted by halogen, trifluoromethyl, $C_1$–$C_4$ alkyl or $C_1$–$C_4$ alkoxy;

$R_2$ is hydrogen;

$R_3$ represents hydrogen, halogen, $C_1$–$C_4$ alkyl or $C_1$–$C_4$ alkoxy;

W represents: a

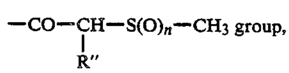

wherein n is 1 or 2 and R" represents hydrogen or methyl; or a

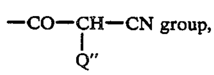

wherein Q" represents hydrogen, $C_2$–$C_3$ alkoxycarbonyl or a —$CONR''_aR''_b$ or —$CSNHR''_b$ group wherein $R''_a$ is hydrogen or methyl and $R''_b$ is $C_1$–$C_6$ alkyl or a —$(CH_2)_{m'}$—$R''_5$ group in which m" is as defined above and $R''_5$ is $C_5$–$C_6$ cycloalkyl or it is phenyl unsubstituted or substituted by one or two substituents chosen independently from halogen, $CF_3$, nitro, amino, methyl and methoxy; and the pharmaceutically acceptable salts thereof.

Examples of particularly preferred compounds of the invention are:

1-methyl-3-methylsulfinylacetyl-3b,4,5,6,-tetrahydro-1H-acenaphthyleno[1,2-c]pyrazole;

1,9-dimethyl-3-methylsulfinylacetyl-1H-acenaphthyleno[1,2-c]pyrazole;

1,6-dimethyl-3-methylsulphinylacetyl-3b,4,5,6-tetrahydro-1H-acenaphthyleno[1,2-c]pyrazole;

2-cyano-3-(1-methyl-1H-acenaphthyleno[1,2-c]pyrazol-3-yl)-N-phenyl-3-oxo-propanamide;

N-benzyl-2-cyano-3-(1-methyl-1H-acenaphthyleno[1,2-c]pyrazol-3-yl)-3-oxo-propanamide;

2-cyano-N-(4-fluoro-phenyl)-3-(1-methyl-3b,4,5,6-tetrahydro-1H-acenaphthyleno[1,2-c]pyrazol-3-yl)-3-oxo-propanamide;

N-benzyl-2-cyano-3-(1-methyl-3b,4,5,6-tetrahydro-1H-acenaphthyleno[1,2-c]pyrazol-3-yl)-3-oxo-propanamide;

2-cyano-3-(9-methoxy-1-methyl-4,5-dihydro-1H,3bH-1-benzopyrano[4,5,6-e,f]cyclopentapyrazol-3-yl)-N-phenyl-3-oxo-propanamide;

9-fluoro-1-methyl-3-methylsulfinylacetyl-4,5-dihydro-1H,3bH-1-benzopyrano[4,5,b-e,f]cyclopentapyrazole;

N-benzyl-2-cyano-3-(9-methoxy-1-methyl-4,5-dihydro-1H,3bH-1-benzopyrano[4,5,6-e,f]cyclopentapyrazol-3-yl)-3-oxo-propanamide;

2-cyano-N-(4-fluoro-phenyl)-3-(9-methoxy-1-methyl-4,5-dihydro-1H,3bH-1-benzopyrano[4,5,6-e,f]cyclopentapyrazol-3-yl)-3-oxo-propanamide;

2-cyano-N-(3-fluoro-phenyl)-3-(9-methoxy-1-methyl-4,5-dihydro-1H,3bH-1-benzopyrano[4,5,6-e,f]cyclopentapyrazol-3-yl)-3-oxo-propanamide;

N-(3-chloro-phenyl)-2-cyano-3-(9-methoxy-1-methyl-4,5-dihydro-1H,3bH-1-benzopyrano[4,5,6-e,f]cyclopentapyrazol-3-yl)-3-oxo-propanamide;

N-benzyl-2-cyano-3-(9-methoxy-1,5-dimethyl-4,5-dihydro-1H,3bH-1-benzopyrano[4,5,6-e,f]cyclopentapyrazol-3-yl)-3-oxo-propanamide;

2-cyano-3-(9-methoxy-1,5-dimethyl-4,5-dihydro-1H,3bH-1-benzo-pyrano[4,5,6-e,f]cyclopentapyrazol-3-yl)-N-phenyl-3-oxo-propanamide;

N-benzyl-2-cyano-3-(9-methoxy-1-methyl-4,5-dihydro-1H,3bH-1-benzothiopyrano[4,5,6-e,f]cyclopentapyrazol-3-yl)-3-oxo-propanamide;

2-cyano-3-(9-methoxy-1-methyl-4,5-dihydro-1H,3bH-1-benzothiopyrano[4,5,6-e,f]cyclopentapyrazol-3-yl)-N-phenyl-3-oxo-propanamide;

2-cyano-N-(4-fluoro-phenyl)-3-(9-methoxy-1-methyl-4,5-dihydro-1H,3bH-1-benzothiopyrano[4,5,6-e,f]cyclopentapyrazol-3-yl)-3-oxo-propanamide;

N-benzyl-2-cyano-3-(9-methoxy-1-methyl-3b,4,5,6-tetrahydro-1H-acenaphthyleno[1,2-c]pyrazol-3-yl)-3-oxo-propanamide;

2-cyano-3-(9-methoxy-1-methyl-3b,4,5,6-tetrahydro-1H-acenaphthyleno[1,2-c]pyrazol-3-yl)-N-phenyl-3-oxo-propanamide;

2-cyano-N-(4-fluoro-phenyl)-3-(9-methoxy-1-methyl-3b,4,5,6-tetrahydro-1H-acenaphthyleno[1,2-c]pyrazol-3-yl)-3-oxo-propanamide;

2-cyano-3-(9-fluoro-1-methyl-4,5-dihydro-1H,3bH-1-benzopyrano[4,5,6-e,f]cyclopentapyrazol-3-yl)-N-phenyl-3-oxo-propanamide;

N-benzyl-2-cyano-3-(9-fluoro-1-methyl-4,5-dihydro-1H,3bH-1-benzopyrano[4,5,6-e,f]cyclopentapyrazol-3-yl)-3-oxo-propanamide;

2-cyano-N-(4-fluoro-phenyl)-3-(9-fluoro-1-methyl-4,5-dihydro-1H,3bH-1-benzopyrano[4,5,6-e,f]cyclopentapyrazol-3-yl)-3-oxo-propanamide;

and the pharmaceutically acceptable salts thereof, in particular the sodium and the potassium salts.

The compounds of formula (I) and the salts thereof can be prepared, for example, by a process comprising:

(A) reacting a compound of formula (II)

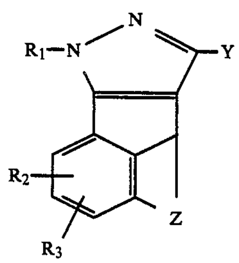

(II)

wherein

Z, $R_1$, $R_2$ and $R_3$ are as defined above and Y is carboxy or a reactive derivative of a carboxy group, with a compound of formula (III)

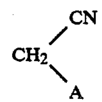

(III)

wherein

A is as Q defined above, except carboxy, so obtaining a compound of formula (I), in which W is a

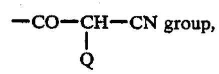

wherein Q is as defined above except carboxy; or (B) reacting a compound of formula (IV)

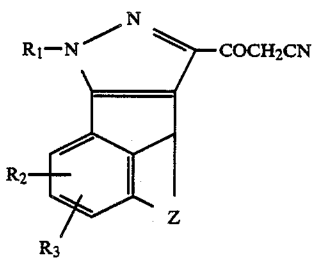

(IV)

wherein

Z, $R_1$, $R_2$ and $R_3$ are as defined above, with a compound of formula (V) or (Va)

$R_b$—N=C=O (V)

$R_b$—N=C=S (Va)

wherein $R_b$ is as defined above, so obtaining a compound of formula (I), in which W is a

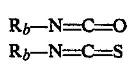

wherein Q is —CONH$R_b$ or a —CSNH$R_b$ group respectively, wherein $R_b$ is as defined above; or (C) reacting a compound of formula (VI)

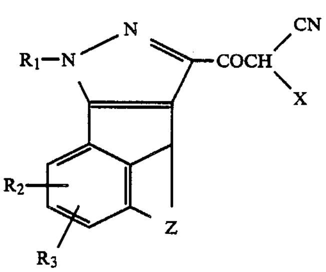

(VI)

wherein

Z, $R_1$, $R_2$ and $R_3$ are as defined above and X is a reactive derivative of a carboxy group, with a compound of formula (VII)

(VII)

wherein $R_a$ and $R_b$ are as defined above, so obtaining compounds of formula (I), in which W is a

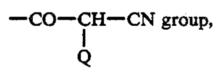

wherein Q is a

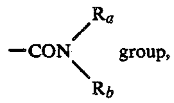

wherein $R_a$ and $R_b$ are as defined above; or (D) reacting a compound of formula (VIII)

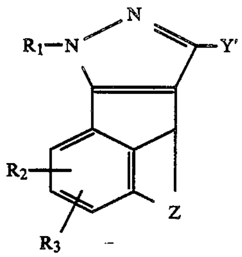

(VIII)

wherein

Z, $R_1$, $R_2$ and $R_3$ are as defined above and Y' is an ester group, with a compound of formula (IX)

$$M^{\oplus\ominus}CH_2—S(O)_n—CH_3 \quad (IX)$$

wherein n is as defined above and M is an alkali metal, so as to obtain a compound of formula (I), in which W is a

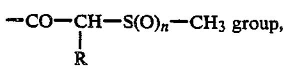

wherein n is as defined above and R is hydrogen; or (E) alkylating a compound of formula (I), in which W is a —CO—CHR—$S(O)_n$—$CH_3$ group, wherein R is hydrogen, and n is as defined above, so as to obtain the corresponding compound of formula (I), in which R is $C_1$-$C_6$ alkyl and n is as defined above; or (F) hydrolizing a compound of formula (I), in which W is a

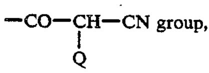

wherein Q is $C_2$-$C_7$ alkoxycarbonyl, so as to obtain the corresponding compound of formula (I), in which W is a

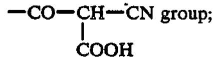

and/or, if desired, converting a compound of formula (I) into another compound of formula (I) and/or, if desired, converting a compound of formula (I) into a pharmaceutically acceptable salt thereof, and/or, if desired, converting a salt of a compound of formula (I) into a free compound, and/or, if desired, separating a mixture of isomers of compounds of formula (I), into the single isomers.

When Y is a reactive derivative of a carboxy group, it is, for example, a halocarbonyl group, preferably a chlorocarbonyl group, or an ester group, preferably a $C_2$-$C_7$ alkoxycarbonyl group, more preferably a $C_2$-$C_3$ alkoxycarbonyl group.

The reaction between a compound of formula (II) wherein Y is carboxy and a compound of formula (III) may be carried out, for example, in the presence of a condensing agent such as diethyl cyanophosphonate, in the presence of a base such as triethylamine, in an inert solvent such as dimethylformamide at a temperature varying between about 0° C. and about 50° C. The reaction between a compound of formula (II) wherein Y is a reactive derivative of a carboxy group and a compound of formula (III) may be carried out, for example, in the presence of a strong base such as sodium hydride, potassium t.butoxide, thallous ethoxide, in an inert solvent such as 1,2-dimethoxyethane, dioxane, dimethylformamide, at a temperature varying between about 0° C. and about 100° C. The reaction between a compound of formula (IV) and a compound of formula (V) or (Va) may be carried out, for example, in the presence of a base such as sodium hydride or triethylamine, in an inert solvent such as toluene, dioxane, tetrahydrofuran, dimethylformamide, at a temperature varying between about 0° C. and about 100° C.

In the compounds of formula (VI), X is, for example, a halocarbonyl group, preferably a chlorocarbonyl group, or a $C_2$-$C_7$ alkoxycarbonyl group, preferably a $C_2$-$C_3$ alkoxycarbonyl group.

The reaction between a compound of formula (VI), wherein X is a halocarbonyl group, and a compound of formula (VII) may be carried out, for example, in an inert solvent such as dichloroethane, dioxane, dimethylformamide, in the presence of pyridine or triethylamine an acid acceptor, at a temperature varying between about 0° C. and about 100° C. The reaction between a compound of formula (VI), wherein X is $C_1$-$C_6$ alkyl ester, and a compound of formula (VII) may be carried out, for example, by heating at the reflux temperature in an aromatic hydrocarbon such as toluene or xylene, preferably distilling off slowly together with the diluent the free $C_1$-$C_6$ alkyl alcohol generated during the reaction.

In the compounds of formula (VIII), Y' is preferably a $C_2$-$C_7$ alkoxycarbonyl group, more preferably a $C_2$-$C_3$ alkoxycarbonyl group.

M is preferably sodium, lithium or potassium.

The reaction between a compound of formula (VIII) and a compound of formula (IX), wherein n is 1, may be carried out, for example, under inert atmosphere, at a temperature varying between about 0° C. and about 50° C., in the presence of excess anhydrous dimethylsulfoxide, which may be optionally diluted with an inert organic solvent such as benzene, dioxane or tetrahydrofuran.

The reaction between a compound of formula (VIII) and a compound of formula (IX), wherein n is 2, may be carried out, for example, under inert atmosphere, at a temperature varying between about 0° C. and about 50° C., in the presence of excess anhydrous dimethylsulfone, which may be optionally diluted with anhydrous dimethylsulfoxide and/or with an inert organic solvent such as benzene, dioxane or tetrahydrofuran.

The alkylation of a compound of formula (I) in which W is a

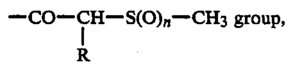

wherein R is hydrogen, so as to obtain the corresponding compound of formula (I), in which W is a

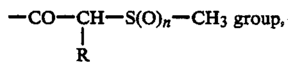

wherein R is $C_1$–$C_6$ alkyl, may be carried out according to known methods, for example, by treatment with sodium or potassium hydride to obtain the carbanion, which in turn is reacted with the suitable $C_1$–$C_6$ alkyl halide, preferably $C_1$–$C_6$ alkyl iodide or bromide, in an inert solvent such as dioxane, tetrahydrofuran or dimethylformamide, under inert atmosphere, at a temperature varying between about 0° C. and about 25° C.

The hydrolysis of a compound of formula (I), in which W is a

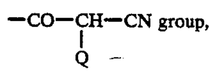

wherein Q is a $C_2$–$C_7$ alkoxycarbonyl group, so as to obtain the corresponding compound of formula (I), in which W is a

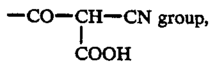

may be carried out, for example, by treatment with aqueous sodium or potassium hydroxide in a solvent such as dioxane or dimethylformamide at a temperature varying between about 0° C. and about 50° C.

A compound of formula (I) may be converted, as stated above, into another compound of formula (I) by known methods; for example, in a compound of formula (I) a nitro group may be converted into an amino group by treatment, for example, with stannous chloride in concentrated hydrochloric acid, using, if necessary, an organic cosolvent such as acetic acid, dioxane, tetrahydrofuran, at a temperature varying between room temperature and about 100° C.

Furthermore, for example, an amino group may be converted into a formylamino or a $C_2$–$C_8$ alkanoylamino group, for example by reacting with formic acid or with a suitable $C_2$–$C_8$ alkanoyl anhydride without any solvent or in an organic solvent such as dioxane, dimethylformamide, tetrahydrofuran, usually in the presence of a base such as pyridine or triethylamine, at a temperature varying between 0° C. and about 100° C.

Furthermore, for example, a compound of formula (I), in which W is a

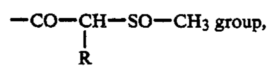

wherein R is as defined above, may be converted into a compound of formula (I), in which W is a

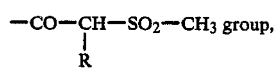

wherein R is as defined above, by treatment with an organic peracid, such as m-chloroperbenzoic acid or peracetic acid, in an inert organic solvent, such as chloroform, dichloroethane, dichloromethane, at a temperature varying between about 0° C. and about 50° C.

Process-variants (B), (C) and (E) described above may be considered as examples of conversions of a compound of formula (I) into another compound of formula (I).

Also the optional salification of a compound of formula (I) as well as the conversion of a salt into the free compound and the separation of a mixture of isomers into the single isomers may be carried out by conventional methods.

The compounds of formula (II), wherein Y is a $C_2$–$C_7$ alkoxycarbonyl group, may be prepared, for example, by reacting a compound of formula (X)

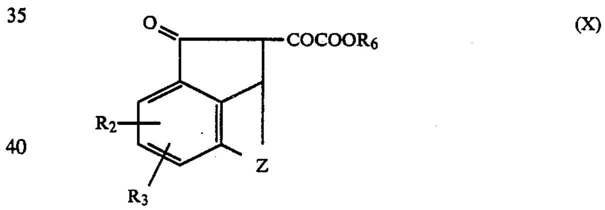

wherein

Z, $R_2$ and $R_3$ are as defined above and $R_6$ is $C_1$–$C_6$-alkyl, preferably $C_1$–$C_2$ alkyl, with a compound of formula (XI)

$$R_1\text{—NHNH}_2 \quad \text{(XI)}$$

wherein $R_1$ is as defined above.

The reaction between a compound of formula (X) and a compound of formula (XI) may be carried out, for example, in a solvent such as a $C_1$–$C_6$ alkyl alcohol, dioxane, tetrahydrofuran, dimethylformamide, acetic acid, at a temperature varying between about 0° C. and about 150° C.

The compounds of formula (II), wherein Y is carboxy may be prepared, for example, by hydrolysis of the corresponding compounds of formula (II) wherein Y is $C_2$–$C_7$ alkoxycarbonyl, according to standard methods well known in the art, for example, by basic hydrolysis, carried out e.g. by treatment with sodium or potassium hydroxide in a solvent such as water, a $C_1$–$C_6$ alkyl alcohol, dioxane, dimethylformamide and their mixtures, at a temperature varying between about 0° C. and about 50° C.

The compounds of formula (II), wherein Y is halocarbonyl, preferably chlorocarbonyl, may be prepared, for example, by reaction of the corresponding compound of formula (II), wherein Y is carboxy, with a suitable acid halide, for example oxalyl chloride, thionyl chloride, $PCl_3$, $PBr_3$, in an inert solvent such as ether, benzene, dichloroethane, dioxane or without any solvent, at a temperature varying between about 0° C. and about 100° C.

The compounds of formula (III) are, in some cases, commercially available products, or may be prepared by methods well known in the art. For example a compound of formula (III), wherein A is a

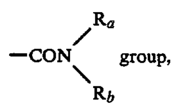

wherein $R_a$ and $R_b$ are as defined above, may be prepared by reacting cyanoacetic acid with a compound of formula (VII) in the presence of a condensing agent such as dicyclohexylcarbodiimide, 1,1-carbonyldiimidazole and the like, in an inert organic solvent such as benzene, dioxane, acetonitrile, at a temperature varying between about 0° C. and about 50° C. The compounds of formula (IV), which are compounds of formula (I) too, may be prepared, for example, by reacting a compound of formula (II), wherein Y is $C_2$–$C_7$ alkoxycarbonyl, with acetonitrile, in the presence of a strong base such as sodium hydride, potassium tert. butoxide, in an inert organic solvent such as benzene, dioxane, tetrahydrofuran, at a temperature varying between about 0° C. and about 100° C.

The compounds of formula (VI), wherein X is $C_2$–$C_7$ alkoxycarbonyl, which are compounds of formula (I) too, may be prepared, for example, by reacting a compound of formula (II) with a compound of formula (XII)

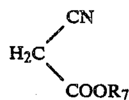

(XII)

wherein $R_7$ is $C_1$–$C_6$ alkyl, using the same experimental conditions as described above for the reaction between a compound of formula (II) and a compound of formula (III).

The compounds of formula (VI), wherein X is halocarbonyl, may be prepared, for example, by basic hydrolysis of a compound of formula (VI), wherein X is $C_2$–$C_7$ alkoxycarbonyl, using, for example, the same experimental conditions described above for the hydrolysis of the compounds of formula (II), wherein Y is $C_2$–$C_7$ alkoxycarbonyl, in order to obtain the corresponding carboxy derivative, which in turn may be transformed into a compound of formula (VI), wherein X is halocarbonyl, preferably chlorocarbonyl, using, for example, the same experimental conditions described above for the preparation of the compounds of formula (II), wherein Y is halocarbonyl. The compounds of formula (VIII) are compounds of formula (II), wherein Y is an ester group and may be prepared, for example, by reacting a compound of formula (X) with a compound of formula (XI), following the same experimental conditions described above for said reaction.

The compounds of formula (IX), wherein n is 1, may be prepared, for example, by reaction of excess anhydrous dimethylsulfoxide with a strong base such as sodium hydride, potassium hydride, potassium tert.butoxide or an alkyl lithium compound, preferably n-butyllithium, at a temperature varying between about 0° C. and about 60° C. under inert atmosphere. If desired an inert organic solvent such as benzene, dioxane or tetrahydrofuran may be present. The compounds of formula (IX), wherein n is 2, may be prepared, for example, by reaction of excess anhydrous dimethylsulfone, optionally diluted with anhydrous dimethylsulfoxide, with a strong base such as sodium hydride, potassium hydride, potassium tert.butoxide or an alkyl lithium compound, preferably n-butyllithium, at a temperature varying between about 0° C. and about 60° C. under inert atmosphere.

If desired an inert organic solvent such as benzene, dioxane or tetrahydrofuran may be present.

The compounds of formula (X) may be prepared by reacting a compound of formula (XIII)

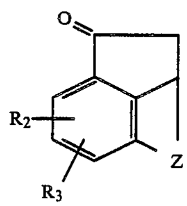

(XIII)

wherein

Z, $R_2$ and $R_3$ are as defined above, with a compound of formula (XIV)

$$\begin{matrix} COOR_6 \\ | \\ COOR'_6 \end{matrix} \quad (XIV)$$

wherein each of $R_6$ and $R'_6$, being the same or different, is $C_1$–$C_6$ alkyl, preferably methyl or ethyl.

The reaction between a compound of formula (XIII) and a compound of formula (XIV) may be carried out, for example, in the presence of a strong base such as sodium methoxide, sodium ethoxide, sodium hydride, potassium tert.butoxide, in an organic solvent such as $C_1$–$C_2$ alkyl alcohol, benzene, dioxane, dimethylformamide, at a temperature varying between about 0° C. and about 100° C.

The compounds of formula (XIII) may be prepared by synthetic methods well known in the art, for example, by methods analogous to those described in Arch. Pharm., 310, 2, 102 (1977); JACS, 62, 432 (1940) and JACS, 78, 3788 (1956).

The compounds of formula (V), (Va), (VII), (XI), (XII) and (XIV) are known products and may be prepared by conventional methods: in some cases they are commercially available products.

When in the compounds of the present invention and in the intermediate products thereof, groups are present, such as $NH_2$ and/or OH, which need to be protected before submitting them to the hereabove illustrated reactions, they may be protected before the reactions take place and then deprotected, according to well known methods in organic chemistry. The compounds of formula (I) possess immunomodulating activity and can be used in particular as immunostimulant agents, e.g. in the treatment of acute and chronic infections of both bacterial and viral origin alone or in association with antibiotic agents and in the treatment of neoplastic diseases, alone or in association with antitumoral agents, in mammals. The immunomodulating activity of the compounds of the invention is proved, for example, by the fact that they are effective in potentiating the cytotoxic activity of the macrophages towards tumor cells in vitro. The following is an example of the experimental procedure which can be used to evaluate this activity: group of 4 mice are treated i.p. with the tested compounds and then, seven days later, pertoneal cells are collected and plated for 2 hours at 37° C. After this period the walls are washed to eliminate the non adherent cells, tumor target cells are then added and the incubation is prolonged for 48 hours. At the end of this period the target cells viability is evaluated by a colorimetric method and quantified at 570 nm.

As preferred example of compounds of formula (I) having immunomodulating activity the following can be mentioned: 1-methyl-3-methylsulfinylacetyl-3b,4,5,6-tetrahydro-1H-acenaphthyleno[1,2-c]pyrazole [internal code FCE 24122]. In view of their high therapeutic index the compounds of the invention can be safely used in medicine.

For example, the approximate acute toxicity ($LD_{50}$) in the mouse of the compound 1-methyl-3-methylsulfinylacetyl-3b,4,5,6-tetrahydro-1H-acenapthyleno[1,2-c]pyrazole, determined per os with single administration of increasing doses and measured on the seventh day after the day of treatment, is higher than 800 mg/kg.

Analogous toxicity data have been found for the other compounds of the invention.

The therapeutic regimen for the different clinical syndromes must be adapted to the type of pathology taking into account, as usual, also the route of administration, the form in which the compound is administered and the age, weight and conditions of the subject involved.

The oral route is employed, in general, for all conditions requiring such compounds. Preference is given to intravenous injection or infusion for the treatment of acute infections. For maintenance regimens the oral or parenteral, e.g. intramuscular or subcutaneous, route is preferred.

For these purposes the compounds of the invention can be administered orally at doses ranging e.g. from about 0.5 to about 10 mg/kg of body weight per day in adult humans. Doses of active compounds ranging e.g. from about 0.2 to about 5 mg/kg of body weight can be used for the parenteral administration in adult humans. Of course, these dosage regimens may be adjusted to provide the optimal therapeutic response.

The nature of the pharmaceutical compositions containing the compounds of this invention in association with pharmaceutically acceptable carriers or diluents will, of course, depend upon the desired route of administration.

The compositions may be formulated in the conventional manner with the usual ingredients. For example, the compounds of the invention may be administered in the form of aqueous or oily solutions or suspensions, tablets, pills, gelatine capsules, syrups, drops or suppositories.

Thus, for oral administration, the pharmaceutical compositions containing the compounds of this invention, are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose carboxymethylcellulose, gum-arabic, tragacanth, polyvinylpyrrolidone; disaggregating agents, such as starches, alginic acid, alginates, sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations.

Said pharmaceutical preparations may be manufactured in known manner, for example by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile aqueous isotonic saline solutions.

The suppositories may contain together with the active compound a pharmaceutically acceptable carrier, e.g. cocoabutter, polyethylene glycol, a polyoxyethylene sorbitan fatty acid ester surfactant or lecithin.

The following examples illustrate but do not limit the invention:

EXAMPLE 1

To a suspension of 50% sodium hydride (7.4 g) in anhydrous dioxane (50 ml), under nitrogen, a solution of diethyl oxalate (34.5 g) in anhydrous dioxane (20 ml) and then a solution of 2a,3,4,5-tetrahydro-acenaphthen-1-one (20.4 g) in anhydrous dioxane (130 ml) are added under stirring at room temperature. The reaction mixture is kept under stirring at a temperature varying between about 25° C. and about 45° C. for 4 hours, then it is diluted with ice water (1500 ml) and acidified to pH=4 with 2N HCl. The precipitate is filtered, washed with water and then purified by treatment with methanol to give 2-ethoxalyl-2a,3,4,5-tetrahydroacenaphthen-1-one (30.8 g), m.p. 92°-94° C., which is reacted with methylhydrazine (5.7 g) in acetic acid (300 ml) at 50° C. for 1 hour.

After cooling the reaction mixture is diluted with ice water and the precipitate filtered and washed with water. After drying under vacuum the product is purified over a $SiO_2$ column using hexane-ethyl acetate=90:10 and then 80:20 as eluent to give 3-ethoxycarbonyl-1- methyl-3b,4,5,6-tetrahydro-1H-acenaphthyleno[1,2-c]pyrazole (19.8 g), m.p. 115°–117° C.

The product so obtained is dissolved in anhydrous tetrahydrofuran (270 ml) and added dropwise, under stirring, at a temperature varying between 10° C. and 20° C., to a solution of methylsulfinyl carbanion obtained by reacting 50% sodium hydride (13.4 g) with anhydrous dimethylsulfoxide (108 ml) at 70° C. for 1 hour. The reaction mixture is kept at room temperature for 1 hour then it is diluted with ice water containing excess $NaH_2PO_4$. The precipitate is filtered, washed with water and then crystallized from dichloromethane/methanol to give 11.8 g of 1-methyl-3-methylsulfinylacetyl-3b,4,5,6-tetrahydro-1H-acenaphthyleno[1,2-c]pyrazole, m.p. 243°–247° C. (dec).

By proceeding analogously, using the suitable hydrazines, the following compounds can be prepared:

1-ethyl-3-methylsulfinylacetyl-3b,4,5,6-tetrahydro-1H-acenaphthyleno[1,2-c]pyrazole;

1-tert.butyl-3-methylsulfinylacetyl-3b,4,5,6-tetrahydro-1H-acenaphthyleno[1,2-c]pyrazole;

9-chloro-1-methyl-3-methylsulfinylacetyl-3b,4,5,6-tetrahydro-1H-acenaphthyleno[1,2-c]pyrazole, m.p. 182°–188° C.;

9-methoxy-1-methyl-3-methylsulfinylacetyl-3b,4,5,6-tetrahydro-1H-acenaphtyleno[1,2-c]pyrazole, m.p. 183°–188° C.;

1,9-dimethyl-3-methylsulfinylacetyl-3b,4,5,6-tetrahydro-1H-acenaphthyleno[1,2-c]pyrazole;

1,6-dimethyl-3-methylsulfinylacetyl-3b,4,5,6-tetrahydro-1H-acenaphthyleno[1,2-c]pyrazole;

1,7,9-trimethyl-3-methylsulfinylacetyl-3b,4,5,6-tetrahydro-1H-acenaphthyleno[1,2-c]pyrazole; and 7-methoxy-1-methyl-3-methylsulfinylacetyl-3b,4,5,6-tetrahydro-1H-acenaphthyleno[1,2-c]pyrazole.

EXAMPLE 2

3-Ethoxycarbonyl-1-phenyl-3b,4,5,6-tetrahydro-1H-acenapthyleno[1,2-c]pyrazole, (7.75 g), m.p. 152°–153° C., prepared according to Example 1, is dissolved in anhydrous tetrahydrofuran (105 ml) and added dropwise under stirring, at a temperature varying between 10° C. and 20° C., to a solution of methylsulfinyl carbanion obtained reacting 50% sodium hydride (4.3 g) and anhydrous dimethylsulfoxide (36 ml) at 70° C. for 1 hour.

The reaction mixture is kept at room temperature for 1 hour then it is diluted with ice water containing excess $NaH_2PO_4$. The precipitate is filtered, washed with water and then crystallized from ethanol to give 4.7 g of 3-methylsulfinylacetyl-1-phenyl-3b,4,5,6-tetrahydro-1H-acenaphthyleno [1,2-c]pyrazole, m.p. 149°–150° C.

By proceeding analogously the following compounds can be prepared:

1-(4-chloro-phenyl)-3-methylsulfinylacetyl-3b, 4, 5, 6-tetrahydro-1H-acenaphthyleno[1,2-c]pyrazole;

1-(4-methoxy-phenyl)-3-methylsulfinylacetyl-3b,4,5,6-tetrahydro-1H-acenaphthyleno[1,2-c]pyrazole;

1-(4-methyl-phenyl)-3-methylsulfinylacetyl-3b,4,5,6-tetrahydro-1H-acenaphthyleno[1,2-c]pyrazole;

1-(3-chloro-phenyl)-3-methylsulfinylacetyl-3b-4,5,6-tetrahydro-1H-acenaphthyleno[1,2-c]pyrazole;

3-methylsulfinylacetyl-1-(3-trifluoromethyl-phenyl)-3b,4,5,6-tetrahydro-1H-acenaphthyleno[1,2-c]pyrazole; ice 3-methylsulfinylacetyl-1-(4-nitro-phenyl)-3b,4,5,6-tetrahydro, 1H-acenaphthyleno[1,2-c]pyrazole;

3-methylsulfinylacetyl-1-(2-pyridyl)-3b,4,5,6-tetrahydro-1H-acenaphthyleno[1,2-c]pyrazole;

1-(4-fluoro-phenyl)-3-methylsulfinylacetyl-3-b,4,5,6-tetrahydro-1H-acenaphthyleno[1,2-c]pyrazole; and 3-methylsulfinylacetyl-1-(3-pyridyl)-3b,4,5,6-tetrahydro-1H-acenaphthyleno[1,2-c]pyrazole.

EXAMPLE 3

By proceeding according to Examples 1 and 2, starting from suitable condensed ketones, the following compounds can be prepared:

1-methyl-3-methylsulfinylacetyl-4,5-dihydro-1H,3bH-cyclopent[cd]indeno[1,2-c]pyrazole;

3-methylsulfinylacetyl-1-phenyl-4,5-dihydro-1H,3bH-cyclopent[cd]indeno[1,2-c]pyrazole;

1-(4-chloro-phenyl)-3-methylsulfinylacetyl-4,5-dihdro-1H,3bH-cyclopent[cd]indeno[1,2-c]pyrazole;

1-(4-fluoro-phenyl)-3-methylsulfinylacetyl-4,5-dihydro-1H-3bH-cyclopent[cd]indeno[1,2-c]pyrazole; and 1-methyl-3-methylsulfinylacetyl-4,5,6,7-tetrahydrobenz[cd]azuleno[1,2-c]pyrazole.

EXAMPLE 4

3-Ethoxycarbonyl-1-methyl-1H-acenaphthyleno[1,2-c]pyrazole (2g), mp 107°–109° C., prepared according to Example 1 starting from acenaphthen-1-one, is dissolved in anhydrous tetrahydrofuran (45 ml) and added dropwise, under stirring, at a temperature varying between 10° C. and 20° C., to a solution of methylsulfinyl carbanion, obtained by reacting 50% sodium hydride (0.7 g) with anhydrous dimethylsulfoxide (30 ml) at 70° C. for 1 hour. The reaction mixture is kept under stirring at room temperature for 1 hour, then is diluted with ice water and acidified with citric acid to pH 4. The precipitate is extracted with ethyl acetate and the organic solution evaporated to dryness in vacuo. The residue is purified over a flash column using toluene/ethanol/diethylamine 100/10/1.5 as eluent. Washings with ethanol give 0.45 g of 1-methyl-3-methylsulfinylacetyl-1H-acenaphthyleno[1,2-c]pyrazole, mp 220°–230° C. dec., NMR (DMSOd6) δppm: 2.76 (s)(3H, —$SO\underline{CH_3}$), 4.16 (s)(3H, =N—$\underline{CH_3}$), 4.57 (s)(2H, —$CO\underline{CH_2}SO$—), 7.5–8.70 (m) (6H, phenyl protons).

By proceeding analogously the following compounds can be prepared:

1.9-dimethyl-3-methylsulfinylacetyl-1H-acenaphthyleno[1,2-c]pyrazole, mp 216°–218° C.;

3-methylsulfinylacetyl-1phenyl-1H-acenaphthyleno[1,2-c]pyrazole;

1-(4-chloro-phenyl)-3-methylsulfinylacetyl-1-H-acenaphthyleno[1,2-c]pyrazole; and 1-(4-fluoro-phenyl)-3-methylsulfinylacetyl-1H-acenaphthyleno[1,2-c]pyrazole.

EXAMPLE 5

A solution of methylsulfonyl carbanion is prepared by reacting 50% sodium hydride (2.88 g) with dimethylsulfone (5.65 g) in anhydrous dimethylsulfoxide (20 ml) under stirring, in an inert atmosphere, at 70° C. for 1 hour. To this solution, after cooling, is added dropwise, under stirring, at a temperature varying between 10° C. and 20° C., 3-ethoxycarbonyl-1-methyl-3b,4, 5, 6-tetrahydro-1H-acenaphthyleno[1,2-c]pyrazole (4.21 g) dissolved in anhydrous tetrahydrofuran (60 ml). The reaction mixture is kept at room temperature for 1 hour then it is diluted with ice water containing excess $NaH_2PO_4$. The precipitate is filtered, washed with water and then crystallized from chloroform/ethanol to give 2.9 g of 1-methyl-3-methylsulfonylacetyl-3b,4,5,6-tetrahydro-1H-acenaphthyleno[1,2-c]pyrazole, mp 226°-228° C.

By proceeding analogously the following compounds can be prepared:

3-methylsulfonylacetyl-1-phenyl-3b,4,5,6-tetrahydro-1H-acenaphthyleno[1,2-c]pyrazole;

1-methyl-3-methylsulfonylacetyl-4,5-dihydro-1H,3bH-cyclopent[cd]indeno[1,2-c]pyrazole; and 1-methyl-3-methylsulfonylacetyl-1H-acenaphthyleno[1,2-c]pyrazole.

EXAMPLE 6

3-Methylsulfinylacetyl-1-(4-nitrophenyl)-3b,4, 5, 6-tetrahydro-1H-acenaphthyleno[1,2-c]pyrazole (4.27 g) is reacted with $SnCl_2.H_2O$ (22.5 g) in 37% HCl (16 ml) and acetic acid (144 ml) under stirring at 40° C. for 5 hours. After cooling the precipitate is filtered and washed with acetic acid and then dissolved in dimethylformamide-2N NaOH 1:1. Dilution with excess aqueous $NaH_2PO_4$ until neutral gives a precipitate which is filtered, washed with water and crystallized from chloroform/ethanol to give 3.05 g of 1-(4-amino-phenyl)-3-methylsulfinylacetyl-3b,4, 5, 6-tetrahydro-1H-acenaphthyleno[1,2-c]pyrazole.

EXAMPLE 7

1(4-amino-phenyl)-3-methylsulfinylacetyl-3b,4, 5, 6-tetrahydro-1H-acenaphthyleno[1,2-c]pyrazole (1.7 g) dissolved in diemthylformamide (25 ml) is reacted with acetic anhydride (5 ml) in the presence of pyridine (2 ml) at room temperature for 20 hours. The reaction mixture is diluted with ice water and the precipitate is filtered and washed with water: crystallization from dimethylformamideethanol gives 1.15 g of 1-(4-acetamido-phenyl)-3-methylsulfinylacetyl-3b,4,5,6-tetrahydro-1H-acenaphthyleno[1,2-c]pyrazole.

EXAMPLE 8

1-Methyl-3-methylsulfinylacetyl-3b,4,5,6-tetrahydro-1H-acenaphthyleno[1,2-c]pyrazole is dissolved by treatment with an equivalent amount of sodium ethoxide in ethanol. The solution is evaporated to dryness and the residue is treated with isopropyl ether and then filtered to give the sodium salt of 1-methyl-3-methylsulfinylacetyl-3b,4,5,6-tetrahydro-1H-acenaphthyleno[1,2-c]pyrazole m.p. 270° C. dec.

EXAMPLE 9

1-Methyl-3-methylsulfinylacetyl-3b,4,5,6-tetrahydro-1H-acenaphthyleno[1,2-c]pyrazole (3.14 g) is dissolved in anhydrous tetrahydrofuran (150 ml) and the solution is added slowly, with stirring, to a suspension of 50% sodium hydride (0.48 g) in anhydrous tetrahydrofuran (25 ml) under nitrogen atmosphere at room temperature. After 30 minutes methyl iodide (2.13 g) is added dropwise and the reaction mixture is kept under stirring for 6 hours at room temperature. The mixture is filtered and the filtrate passed through a $SiO_2$ column using tetrahydrofuran as eluent, then the purified solution is evaporated to dryness in vacuo and the residue crystallized from dichloromethane/isopropyl ether to give 1.4 g of (RS)-1-methyl-3-(2-methylsulfinyl-propanoyl)-3b,4,5,6-tetrahydro-1H-acenaphthyleno[1,2-c]pyrazole, mp 142°-158° C.

EXAMPLE 10

To a suspension of 50% sodium hydride (7.4 g) in anhydrous dioxane (50 ml), under nitrogen, a solution of diethyl oxalate (34.5 g) in anhydrous dioxane (20 ml) and then a solution of 2a,3,4,5-tetrahydro-acenaphthen-1-one (20.4 g) in anhydrous dioxane (130 ml) are added under stirring at room temperature. The reaction mixture is kept under stirring at a temperature varying between about 25° C. and about 45° C. for 4 hours, then it is diluted with ice water (1500 ml) and acidified to pH 4 with 2N HCl. The precipitate is filtered, washed with water and then purified by treatment with methanol to give 2-ethoxalyl-2a,3,4,5-tetrahydro-acenaphthen-1-one (30.8 g), m.p. 92°-94° C., wich is reacted with methylhydrazine (5.7 g) in acetic acid (300 ml) at 50° C. for 1 hour.

After cooling the reaction mixture is diluted with ice water and the precipitate filtered and washed with water. After drying under vacuum the product is purified over a $SiO_2$ column using hexane/ethyl acetate 90:10 and then 80:20 as eluent to give 3-ethoxycarbonyl-1-methyl-3b,4,5,6-tetrahydro-1H-acenaphthyleno[1,2-c]pyrazole (19.8 g), m.p. 115°-117° C. This compound (3.2 g) is then reacted with acetonitrile (48 ml) in dioxane (22 ml) in the presence of 50% sodium hydride (1.1 g) under stirring at 60° C. for 45 minutes. After cooling the reaction mixture is diluted with ice water and acidified to pH 4 with citric acid. The precipitate is filtered and washed with water until neutral. Crystallization from methanol gives 2.1 g of 3-(1-methyl-3b,4,5,6-tetrahydro-1H-acenapthyleno[1,2-c]pyrazol-3-yl)-3-oxo-propanenitrile, m.p. 225°-227° C.

By proceeding analogously the following compounds can be prepared:

3-(1-phenyl-3b,4,5,6-tetrahydro-1H-acenaphthyleno[1,2-c]pyrazol-3-yl)-3-oxo-propanenitrile, m.p. 143°-146° C.;

3-(9-chloro-1-methyl-3b,4,5,6-tetrahydro-1H-acenaphthyleno[1,2-c]pyrazol-3-yl)-3-oxo-propanenitrile;

3-(9-methoxy-1-methyl-3b,4,5,6-tetrahydro-1H-acenapthyleno[1,2-c]pyrazol-3-yl)-3-oxo-propanenitrile; mp 230°-233° C.;

3-(1,9-dimethyl-3b,4,5,6-tetrahydro-1H-acenaphthyleno[1,2-c]pyrazol-3-yl)-3-oxo-propanenitrile; and 3-(1-ethyl-3b,4,5,6-tetrahydro-1H-acenaphthyleno[1,2-c]pyrazol-3-yl)-3-oxo-propanenitrile.

EXAMPLE 11

3-(1-Methyl-3b,4,5,6-tetrahydro-1H-acenaphthyleno[1,2-c]pyrazol-3-yl)-3-oxo-propanenitrile (1.95 g) is reacted with phenyl isocyanate (0.8 g) in the presence of triethylamine (0.75 g) in dimethylformamide (20 ml) under stirring at 25°-30° C. for 90 minutes. The reaction mixture is diluted with ice water, acidified to pH 2 with HCl and the precipitate is filtered and washed with water. Crystallization from dichloromethane/methanol gives 1.8 g of 2-cyano-3-(1-methyl-3b,4,5,6-tetrahydro-1H-acenaphthyleno[1,2-c]pyrazol-3-yl)-N-phenyl-3-oxo-propanamide, m.p. 267°-270° C., NMR ($DMSO-d_6+CDCl_3$) δ ppm: 3.61 (dd) (1H, C-3b proton), 4.18 (s)(3H, $CH_3$), 6.9-7.7 (m) (8H, aromatic protons), 9.95 (bs) (1H, —CONH—).

By proceeding analogously the following compounds can be prepared:

2-cyano-3-(1-phenyl-3b,4,5,6-tetrahydro-1H-acenaphthyleno[1,2-c]pyrazol-3-yl)-N-phenyl-3-oxo-propanamide, m.p. 250°-252° C.;

2-cyano-3-(9-chloro-1-methyl-3b,4,5,6-tetrahydro-1H-acenaphthyleno[1,2-c]pyrazol-3-yl)-N-phenyl-3-oxo-propanamide, mp 275°-278° C.;

2-cyano-3-(9-methoxy-1-methyl-3b,4,5,6-tetrahydro-1H-acenapthyleno[1,2-c]pyrazol-3-yl)-N-phenyl-3-oxo-propanamide, m.p. 275°-277° C.;

2-cyano-3-(1,6-dimethyl-3b,4,5,6-tetrahydro-1H-acenapthyleno[1,2-c]pyrazol-3-yl)-N-phenyl-3-oxo-propanamide;

2-cyano-3-(1-ethyl-3b,4,5,6-tetrahydro-1H-acenaphthyleno[1,2-c]pyrazol-3-yl-N-phenyl-3-oxo-propanamide;

2-cyano-3-(7-methoxy-1-methyl-3b,4,5,6-tetrahydro-1H-acenaphthyleno[1,2-c]pyrazol-3-yl)-N-phenyl-3-oxopropanamide; and 2-cyano-3-(1-methyl-4,5,6,7-tetrahydro-benz[c-d]azuleno[1,2-c]pyrazol-3-yl)-N-phenyl-3-oxo-propanamide.

EXAMPLE 12

By proceeding according to Example 11, using the suitable isocyanates, the following compounds can be prepared:

2-cyano-N-cyclohexyl-3-(1-methyl-3b,4,5,6-tetrahydro-1H-acenaphthyleno[1,2-c]pyrazol-3-yl)-3-oxo-propanamide;

N-(4-chloro-phenyl)-2-cyano-3-(1-methyl-3b,4,5,6-tetrahydro-1H-acenaphthyleno[1,2-c]pyrazol-3yl)-3-oxopropanamide; mp 275°-278° C.;

N-(3-chloro-phenyl)-2-cyano-3-(1-methyl-3b,4,5,6-tetrahydro-1H-acenaphthyleno[1,2-c]pyrazol-3-yl)-3-oxopropanamide, m.p. 270°-272° C.;

2-cyano-N-(4-fluoro-phenyl)-3-(1-methyl-3b,4,5,6-tetrahydro-1H-acenaphthyleno[1,2-c]pyrazol-3-yl)-3-oxopropanamide, m.p. 289°-290° C.;

2-cyano-N-(4-methoxy-phenyl)-3-(1-methyl-3b,4,5,6-tetrahydro-1H-acenaphthylene[1,2-c]pyrazol-3-yl)-3-oxopropanamide, m.p. 258°-261° C.;

2-cyano-N-(4-methyl-phenyl)-3-(1-methyl-3b,4,5,6-tetrahydro-1H-acenaphthylene[1,2-c]pyrazol-3-yl)-3-oxopropanamide;

2-cyano-3-(1-methyl-3b,4,5,6-tetrahydro-1H-acenaphthyleno[1,2-c]pyrazol-3-yl-N-(3-trifluoromethyl-phenyl)-3-oxopropanamide, m.p. 275°-276° C.;

N-butyl-2-cyano-3-(1-methyl-3b,4,5,6-tetrahydro-1H-acenaphthyleno[1,2-c]pyrazol-3-yl)-3-oxo-propanamide; mp 300° C. dec.;

2-cyano-N-(3-fluoro-phenyl)-3-(1-methyl-3b,4,5,6-tetrahydro-1H-acenaphthyleno[1,2-c]pyrazol-3-yl)-3-oxopropanamide;

2-cyano-N-(3-methoxy-phenyl)-3-(1-methyl-3b,4,5,6-tetrahydro-1H-acenaphthyleno[1,2-c]pyrazol-3-yl)-3-oxopropanamide;

2-cyano-N-(3-nitro-phenyl)-3-(1-methyl-3b,4,5,6-tetrahydro-1H-acenaphthyleno[1,2-c]pyrazol-3-yl)-3-oxopropanamide, m.p. 251°-253° C.;

N-(3-bromo-phenyl)-2-cyano-3-(1-methyl-3b,4,5,6-tetrahydro-1H-acenaphthyleno[1,2-c]pyrazol-3-yl)-3-oxopropanamide;

N-(3-chloro-phenyl)-2-cyano-3-(9-methoxy-1-methyl-3b,4,5,6-tetrahydro-1H-acenaphthyleno[1,2-c]pyrazol-3-yl)-3-oxo-propanamide;

2-cyano-N-(4-fluoro-phenyl)-3-(9-methoxy-1-methyl-3b,4,5,6-tetrahydro-1H-acenaphthyleno[1,2-c]pyrazol-3-yl)-3-oxo-propanamide;

2-cyano-N-(3-fluoro-phenyl)-3-(9-methoxy-1-methyl-3b,4,5,6-tetrahydro-1H-acenaphthyleno[1,2-c]pyrazol-3-yl)-3-oxo-propanamide;

N-benzyl-2-cyano-3-(9-methoxy-1-methyl-3b,4,5,6-tetrahydro-1H-acenaphthyleno[1,2-c]pyrazol-3-yl)-3-oxopropanamide;

2-cyano-3-(9-methoxy-1-methyl-3b,4,5,6-tetrahydro-1H-acenaphthyleno[1,2-c]pyrazol-3-yl)-N-(3-methyl-phenyl)-3-oxo-propanamide;

N-(2-chloro-phenyl)-2-cyano-3-(1-methyl-3b,4,5,6-tetrahydro-1H-acenaphthyleno[1,2-c]pyrazol-3-yl)-3-oxo-propanamide; 2-cyano-N-(3-methyl-phenyl)-3-(1-methyl-3b,4,5,6-tetrahydro-1H-acenaphthyleno[1,2]pyrazol-3-yl)-3-oxopropanamide, m.p. 245°-250° C.;

2-cyano-N-ethyl-3-(1-methyl-3b,4,5,6-tetrahydro-1H-acenaphthyleno[1,2-c]pyrazol-3-yl)-3-oxo-propanamide;

N-benzyl-2-cyano-3-(1-methyl-3b,4,5,6-tetrahydro-1H-acenaphthyleno[1,2-c]pyrazol-3-yl)-3-oxo-propanamide, m.p. 266°-8° C.;

N-tert.butyl-2-cyano-3-(1-methyl-3b,4,5,6-tetrahydro-1H-acenaphthyleno[1,2-c]pyrazol-3-yl)-3-oxo-propanamide; and 2-cyano-3-(1-methyl-3b,4,5,6-tetrahydro-1H-acenaphthyleno[1,2-c]pyrazol-3-yl)-N-methyl-3-oxo-propanamide.

EXAMPLE 13

3-(1-Methyl-3b,4,5,6-tetrahydro-1H-acenaphthyleno[1,2-c]pyrazol-3-yl)-3-oxo-propanenitrile (1.4 g) is reacted with phenyl isothiocyanate (1 g) in the presence of triethylamine (0.56 g) in dimethylformamide (15 ml) under stirring at 50° C. for 1 hour. After cooling, the reaction mixture is diluted with ice water and acidified to pH 1 with 2N HCl. The precipitate is extracted with chloroform and the organic solution is washed with N HCl and then with water until neutral. After evaporation of the solvent in vacuo the residue is crystallized from $CH_2Cl_2$/isopropyl alcohol to give 1.2 g of 2-cyano-3-(1-methyl-3b,4,5,6-tetrahydro-1H-acenaphthyleno[1,2-c]pyrazol-3-yl)-N-phenyl-3-oxothio-propanamide.

By proceeding analogously the following compounds can be prepared:

2-cyano-3-(1-ethyl-3b,4,5,6-tetrahydro-1H-acenaphthyleno[1,2-c]pyrazol-3-yl)-N-phenyl-3-oxo-thio-propanamide;

2-cyano-3-(9-chloro-1-methyl-3b,4,5,6-tetrahydro-1H-acenaphthyleno[1,2-c]pyrazol-3-yl)-N-phenyl-3-oxo-thiopropanamide;

2-cyano-3-(9-methoxy-1-methyl-3b,4,5,6-tetrahydro-1H-acenaphthyleno[1,2-c]pyrazol-3-yl)-N-phenyl-3-oxothiopropanamide; and 2-cyano-3-(1,9-dimethyl-3b,4,5,6-tetrahydro-1H-acenaphthyleno[1,2-c]pyrazol-3-yl)-N-phenyl-3-oxo-thiopropanamide.

EXAMPLE 14

Acenaphthen-1-one (JACS, 62, 432, 1940) (4.1 g) is reacted with diethyl oxalate (4.2 g) in anhydrous ethanol (280 ml) containing sodium ethoxide (from 0.66 g of sodium) at room temperature for 2 hours. The precipitate is filtered and washed with hexane, then is dissolved in water. The aqueous solution is acidified to pH 4 with citric acid and the precipitate is filtered and washed with water. Crystallization from chloroform-hexane gives 2-ethoxalylacenaphthen-1-one, m.p. 101°-103° C. (5.1 g), which is reacted with methylhydrazide (1.3 g) in acetic acid (110 ml) at 60° C. for 4 hours. After cooling the reaction mixture is diluted with ice water and extracted with ethyl acetate.

The organic solution is evaporated to dryness in vacuo and the residue is purified over a "flash column" using hexane/ethyl acetate 1:1 as eluent to give 3-ethoxycarbonyl-1-methyl-1H-acenaphthyleno[1,2-c]pyrazole, m.p. 107°-109° C. (3 g), which is hydrolized by heating with 1% KOH solution in 95% ethanol (5.5 ml) at reflux temperature for 30 minutes. The reaction mixture is diluted with ice water and acidified to pH 3 with 37% HCl. The precipitate is filtered, washed with water and crystallized from chloroform/ethanol to yield 1-methyl-1H-acenaphthyleno[1,2-c]pyrazole-3-carboxylic acid, m.p. 220° C. dec. (2.4 g), which is reacted with thionyl chloride (1.3 ml) in dioxane (150 ml) at reflux temperature for 2 hours. After cooling the solution is evaporated to dryness in vacuo to give 1-methyl-1H-acenaphthylene[1,2-c]pyrazole-3-carbonyl chloride (2.6 g). The crude product is dissolved in anhydrous dioxane (55 ml) and reacted for 20 minutes under stirring at room temperature with cyanoacetanilide carbanion (1.7 g), prepared by treatment with 50% sodium hydride (0.62 g) in anhydrous dimethylformamide (30 ml) at room temperature. The reaction mixture is then diluted with ice water and acidified to pH 1 with N HCl.

The precipitate is filtered and dissolved in chloroform, then the organic solution is washed with N HCl and water until neutral. Crystallization from chloroform-ethanol yields 3.1 g of 2-cyano-3-(1-methyl-1H-acenaphthyleno[1,2-c]pyrazol-3-yl)-N-phenyl-3-oxo-propanamide, m.p. 275°-278° C., NMR ($CDCl_3$) $\delta$ ppm: 4.30 (s) (3H, —$CH_3$), 7.10-8.20 (m) (12H), phenyl protons+—CONH—), 16, 5 (s) (1H, —OH enol).

By proceeding analogously the following compounds can be prepared:

- 2-cyano-3-(1-methyl-1H-acenaphtyleno[1,2-c]pyrazol-3-yl)-N-methyl-N-phenyl-3-oxo-propanamide;
- 2-cyano-3-(1-methyl-1H-acenaphthyleno[1,2-c]pyrazol-3-yl)-N-(2,6-dimethyl-phenyl)-3-oxo-propanamide;
- 2-cyano-3-(1-methyl-1H-acenaphthyleno[1,2-c]pyrazol-3-yl)-N-(2-pyridyl)-3-oxo-propanamide;
- 2-cyano-3-(1-methyl-3b,4,5,6-tetrahydro-1H-acenaphthyleno[1,2-c]pyrazol-3-yl)-N-phenyl-3-oxo-propanamide, m.p. 267°-270° C.;
- N-benzyl-2-cyano-3-(1-methyl-1H-acenaphthyleno[1,2-c]pyrazol-3-yl)-3-oxo-propanamide;
- 2-cyano-3-(1-methyl-3b,4,5,6-tetrahydro-1H-acenapthyleno[1,2-c]pyrazol-3-yl)-N-methyl-N-phenyl-3-oxo-propanamide;
- 2-cyano-3-(1-methyl-3b,4,5,6-tetrahydro-1H-acenaphthyleno[1,2-c]pyrazol-3-yl)-N-(2,6-dimethyl-phenyl)-3-oxo-propanamide;
- 2-cyano-N-(4-dimethylamino-phenyl)-3-(1-methyl-3b,4,5,6-tetrahydro-1H-acenaphthyleno[1,2-c]pyrazol-3-yl)-3-oxo-propanamide;
- 2-cyano-N-(4-hydroxy-phenyl)-3-(1-methyl-3b,4,5,6-tetrahydro-1H-acenaphthyleno[1,2-c]pyrazol-3-yl)-3-oxo-propanamide;
- 2-cyano-3-(1-methyl-3b,4,5,6-tetrahydro-1H-acenapthyleno[1,2-c]pyrazol-3-yl)-N-(2-pyridyl)-3-oxo-propanamide; and
- 2-cyano-3-(1-methyl-3b,4,5,6-tetrahydro-1H-acenaphthyleno[1,2-c]pyrazol-3-yl)-N-(3-pyridyl)-3-oxo-propanamide.

EXAMPLE 15

Ethyl cyanoacetate (1.2 g) is treated with 50% sodium hydride (0.62 g) in anhydrous dimethylformamide at room temperature until the effervescence subsides. To this solution 1-methyl-3b,4,5,6-tetrahydro-1H-acenaphthyleno([1,2-c]pyrazole-3-carbonyl chloride (2.6 g), prepared according to Example 14, dissolved in anhydrous dioxane (50 ml) is added under stirring at room temperature. The reaction mixture is allowed to react for 2 hours, then is diluted with ice water and acidified to pH1 with 37% HCl. The gummy precipitate is extracted with ethyl acetate and the organic solution washed with N HCl and water, then evaporated to dryness in vacuo. The residue is purified over $SiO_2$ column, using chloroform/methanol as eluent, to give 1.1 g of 2-cyano-3-(1-methyl-3b,4,5,6-tetrahydro-1H-acenaphthyleno[1,2-c]pyrazol-3-yl)-3-oxo-propanoic acid, ethyl ester.

By proceeding analogously the compound 2-cyano-3-(1-methyl-1H-acenaphthyleno[1,2-c]pyrazol-3-yl)-3-oxo-propanoic acid, ethyl ester can be obtained.

EXAMPLE 16

2-Cyano-3-(1-methyl-3b,4,5,6-tetrahydro-1H-acenaphthyleno[1,2-c]pyrazol-3-yl)-3-oxo-propanoic acid, ethyl ester (1 g) is reacted with aniline (1.4 g) in xylene (100 ml) at the reflux temperature for 48 hours. After cooling the precipitate is filtered and washed with xylene, then crystallized from dichloromethane/methanol to give 0.6 g of 2-cyano-3-(1-methyl-3b,4,5,6-tetrahydro-1H-acenaphthyleno[1,2-c]pyrazol-3-yl)-N-phenyl-3-oxo-propanamide, m.p. 267°-270° C.

By proceeding analogously the following compounds can be prepared:

- 2-cyano-3-(1-methyl-3b,4,5,6-tetrahydro-1H-acenaphthyleno[1,2-c]pyrazol-3-yl)-N-(4-trifluoromethyl-phenyl)-3-oxo-propanamide; and
- 2-cyano-3-(1-methyl-1H-acenaphthyleno[1,2-c]pyrazol-3-yl)-N-phenyl-3-oxo-propanamide, m.p. 275°-278° C.

EXAMPLE 17

2-Cyano-3-(1-methyl-3b,4,5,6-tetrahydro-1H-acenaphthyleno[1,2-c]pyrazol-3-yl)-N-phenyl-3-oxo-propanamide is dissolved by treatment with an equivalent amount of sodium ethoxide in ethanol. The solution is evaporated to dryness and the residue is treated with isopropyl ether and then filtered to give the sodium salt of 2-cyano-3-(1-methyl-3b,4,5,6-tetrahydro-1H-acenaphthyleno[1,2-c]pyrazol-3-yl)-N-phenyl-3-oxo-propanamide, m.p. >300° C.

By proceeding analogously the sodium salts of the following compounds can be prepared:

- 2-cyano-3-(9-methoxy-1-methyl-3b,4,5,6-tetrahydro-1H-acenaphthyleno[1,2-c]pyrazol-3-yl)-N-phenyl-3-oxo-propanamide; and
- 2-cyano-3-(1-methyl-1H-acenaphthyleno[1,2-c]pyrazol-3-yl)-N-phenyl-3-oxo-propanamide.

EXAMPLE 18

To a solution of 4-hydroxy-6-methoxy-2,3-dihydro-4H-1-benzopyran (20 g) dissolved in benzene (150 ml), phosphorus trichloride (16.7 g) diluted in benzene (50 ml) is cautiously added under stirring at a temperature maintained below 20° C. by external cooling, then the reaction mixture is kept at 50° C. for 1 hour. After cooling the solution is poured into a 10% $NaHCO_3$ solution (1 l) containing ice, under stirring, then the organic phase is separated and the aqueous phase extracted with ethyl acetate. The organic solutions are evaporated to dryness in vacuo to yield crude 4-chloro-6-methoxy-2,3-dihydro-4H-1-benzopyran as brown oil (21.5 g), which is dissolved in anhydrous dimethylformamide (90 ml) and added under stirring at about 20° C. to a solution of diethylmalonate carbanion (prepared from 19.1 g of diethylmalonate and 5.7 g of 50% sodium hydride) in anhydrous dimethylformamide (30 ml). The reaction mixture is heated at 70° C. for 7 hours, then is cooled at room temperature and diluted with ice water containing excess $NaH_2PO_4$.

The precipitate is extracted with ethyl acetate and the organic phase is evaporated to dryness in vacuo to yield crude (6-methoxy-2,3-dihydro-4H-1-benzopyran-4-yl)-malonic acid diethylester as brown oil (34 g), which hydrolized by treatment with KOH (12 g) in 90% ethanol (145 ml) at the reflux temperature for 3 hours. After cooling the reaction mixture is diluted with ice water and acidified to pH 2 with 23% HCl. The precipitate is extracted with ethyl acetate, washed with water and the organic solution evaporated to dryness in vacuo. Crystallization from isopropyl ether gives (6-methoxy-2,3-dihydro-4H-1-benzopyran-4-yl)malonic acid, m.p. 143°-145° C. (16 g), which is heated in glacial acetic acid (50 ml) at reflux temperature for 7 hours until the effervescence subsides. The reaction mixture is evaporated to dryness in vacuo and the crystalline residue is crumbled by treatment with hexane to yield (6-methoxy-2,3-dihydro-4H-1-benzopyran-4-yl)-acetic acid, m.p. 80°-83° C. (12.4 g), which is dissolved in trifluoroacetic acid (22.5 ml) and treated cautiously with trifluoroacetic anhydride (15.5 ml), added dropwise at a temperature below 20° C. with external cooling. The reaction mixture is kept at room temperature for 7 hours, then is poured in crushed ice. The precipitate is filtered and washed with water until neutral, then dissolved in ethyl acetate. The organic solution is washed with 5% $NaHCO_3$ and water and finally evaporated to dryness in vacuo. The residue is purified over a "flash" column, using hexane/ethyl acetate 2:1 as eluent, to give 6-methoxy-2,3,3a,4-tetrahydro-5H-cyclopenta[de]-1-benzopyran-5-one, m.p. 122°-124° C. (6.7 g) which is dissolved together with diethyl oxalate (9.5 g) in anhydrous dioxane (100 ml). The solution is added under stirring to a suspension of 50% sodium hydride (2.3 g) in anhydrous dioxane (50 ml) at room temperature, then the reaction mixture is kept under stirring at the reflux temperature for 20 hours. After cooling the solution is diluted in ice water in the presence of excess $NaH_2PO_4$, then is acidified to pH 3 with 2N HCl. The precipitate is filtered, then dissolved in ethyl acetate and the solution washed with water and evaporated to dryness in vacuo. The residue is crumbled by treatment with methanol to give 4-ethoxalyl-6-methoxy-2,3,3a,4-tetrahydro-5H-cyclopenta[d e]-1-benzopyran-5-one, m.p. 104°-106° C. (10.1 g), which is reacted with methylhydrazine (1.7 g) in acetic acid (100 ml) at 50° C. for 45 minutes. After cooling the reaction mixture is diluted with ice water and the precipitate extracted with ethyl acetate. The organic phase is washed with water and evaporated to dryness in vacuo. The residue is crumbled by treatment with methanol (40 ml) to yield 3-ethoxycarbonyl-9-methoxy-1-methyl-4,5-dihydro-1H,3bH-1-benzopyrano[4,5,6-e,f]cyclopentapyrazole, m.p. 112°-114° C. (7.8 g). The product obtained (1.1 g) is dissolved in anhydrous tetrahydrofuran (16 ml) and added dropwise under stirring, at a temperature varying between 10° C. and 20° C., to a solution of methylsulfinyl carbanion, obtained by reacting 50% of sodium hydride (0.67 g) with anhydrous dimethylsulfoxide (6ml) at 70° C. for 1 hour. The reaction mixture is kept at room temperature for 45 min., then is diluted with ice water containing excess $NaH_2PO_4$. The precipitate is filtered, washed with water and purified over a "flash" column using chloroform/methanol 100:1.5 as eluent. Crystallization from $CH_2Cl_2$/methanol gives 0.8 g of 9-methoxy-1-methyl-3-methylsulfinylacetyl-4,5-dihydro-1H,3bH-1-benzopyrano[4,5,6-e,f]cyclopentapyrazole, m.p. 230°-235° C. dec, NMR ($CDCl_3$)$\delta$ ppm: 1.20-1.80 (m) (1H, C-4 proton), 2.60-2.95 (m) (1H, C-4 proton), 2.89 (s) (3H, —$SOCH_3$), 3.89 (dd) (1H, C-3b proton), 3.92 (s) (3H, —$OCH_3$), 4.30 (s) (3H, $>NCH_3$), 4.20-4.80 (m) (4H, —$COCH_2SO$— and C-5 protons).

By proceeding analogously the following compounds can be prepared:

1-methyl-3-methylsulfinylacetyl-4,5-dihydro-1H,3bH-1-benzopyrano[4,5,6-e,f]cyclopentapyrazole;

9-chloro-1-methyl-3-methylsulfinylacetyl-4,5-dihydro-1H,3bH-1-benzopyrano[4,5,6-e,f]cyclopentapyrazole, m.p. 214°-218° C.;

1,9-dimethyl-3-methylsulfinylacetyl-4,5-dihydro-1H,3bH-1-benzopyrano[4,5,6-e,f]cyclopentapyrazole;

1-ethyl-9-methoxy-3-methylsulfinylacetyl-4,5-dihydro-1H,3bH-1-benzopyrano[4,5,6-e,f]cyclopentapyrazole;

9-methoxy-3-methylsulfinylacetyl-1-phenyl-4,5-dihydro-1H,3bH-1-benzopyrano[4,5,6-e,f]cyclopentapyrazole;

7-methoxy-1-methyl-3-methylsulfinylacetyl-4,5-dihydro-1H,3bH-1-benzopyrano[4,5,6-e,f]cyclopentapyrazole;

9-fluoro-1-methyl-3-methylsulfinylacetyl-4,5-dihydro-1H,3bH-1-benzopyrano[4,5,6-e,f]cyclopentapyrazole; and 9-fluoro-1,5-dimethyl-3-methylsulfinylacetyl-4,5-dihydro-1H,3bH-1-benzopyrano[4,5,6-e,f]cyclopentapyrazole.

EXAMPLE 19

By proceeding according to Example 18, starting from suitable 4-hydroxy-2,3-dihydro-4H-1-benzothiopyrans, the following compounds can be prepared:

1-methyl-3-methylsulfinylacetyl-4,5-dihydro-1H,3bH-1-benzothiopyrano[4,5,6-e,f]cyclopentapyrazole;

9-methoxy-1-methyl-3-methylsulfinylacetyl-4,5-dihydro-1H,3bH-1-benzothiopyrano[4,5,6-e,f]cyclopentapyrazole;

9-chloro-1-methyl-3-methylsulfinylacetyl-4,5-dihydro-1H,3bH-1-benzothiopyrano[4,5,6-e,f]cyclopentapyrazole;

1,9-dimethyl-3-methylsulfinylacetyl-4,5-dihydro-1H,3bH-1-benzothiopyrano[4,5,6-e,f]cyclopentapyrazole;

9-methoxy-3-methylsulfinylacetyl-1-phenyl-4,5-dihydro-1H,3bH-1-benzothiopyrano[4,5,6-e,f]cyclopentapyrazole;

9-methoxy-1-methyl-3-methylsulfinylacetyl-4,5-dihydro-1H,3bH-1-benzothiopyrano[4,5,6-e,f]cyclopentapyrazole-6,6-dioxide; and 9-fluoro-1-methyl-3-methylsulfinylacetyl-4,5-dihydro-1H,3bH-1-benzothiopyrano[4,5,6-e,f]cyclopentapyrazole.

EXAMPLE 20

A solution of methylsulfonyl carbanion is prepared by reacting 50% sodium hydride (2.88 g) with dimethylsulfone (5.65 g) in anhydrous dimethylsulfoxide (20 ml) under stirring, in an inert atmosphere, at 70° C. for 1 hour. To this solution, after cooling, is added dropwise, under stirring, at a temperature varying between 10° C. and 20° C., 3-ethoxycarbonyl-9-methoxy-1-methyl-4,5-dihydro-1H,3bH-1-benzopyrano[4,5,6-e,f]cyclopentapyrazole (4.6 g), prepared according to Ex. 18. dissolved in anhydrous tetrahydrofuran (60 ml). The reaction mixture is kept at room temperature for 20 hours, then is diluted with ice water containing excess $NaH_2PO_4$. The precipitate is filtered, washed with water and then purified over a $SiO_2$ column using chloroform/ethanol 99:1 as eluent. Crystallization from $CH_2Cl_2$/methanol gives 3.2 g of 9-methoxy-1-methyl-3-methylsulfonylacetyl-4,5-dihydro-1H,3bH-1-benzopyrano[4,5,6-e,f]cyclopentapyrazole.

By proceeding analagously the following compounds can be prepared:

1-methyl-3-methylsulfonylacetyl-4,5-dihydro-1H,3bH-1-benzopyrano[4,5,6-e,f]cyclopentapyrazole;

9-chloro-1-methyl-3-methylsulfonylacetyl-4,5-dihydro-1H,3bH-1-benzopyrano[4,5,6-e,f]cyclopentapyrazole;

1,9-dimethyl-3-methylsulfonylacetyl-4,5-dihydro-1H,3bH-1-benzopyrano[4,5,6-e,f]cyclopentapyrazole;

1-methyl-3-methylsulfonylacetyl-4,5-dihydro-1H,3bH-1-benzothiopyrano[4,5,6-e,f]cyclopentapyrazole;

9-methoxy-1-methyl-3-methylsulfonylacetyl-4,5-dihydro-1H,3bH-1-benzothiopyrano[4,5,6-e,f]cyclopentapyrazole;

9-chloro-1-methyl-3-methylsulfonylacetyl-4,5-dihydro-1H,3bH-1-benzothiopyrano[4,5,6-e,f]cyclopentapyrazole; and 1,9-dimethyl-3-methylsulfonylacetyl-4,5-dihydro-1H,3bH-1-benzothiopyrano[4,5,6-e,f]cyclopentapyrazole.

EXAMPLE 21

3-Ethoxycarbonyl-9-methoxy-1-methyl-4,5-dihydro-1H,3bH-1-benzopyrano[4,5,6-e,f]cyclopentapyrazole (4.3 g), prepared according to Example 18, suspended in ethanol (160 ml) is treated with a solution of KOH (1.9 g) in water (12.5 ml). The reaction mixture is heated at the reflux temperature for 30'. After cooling the solution is diluted with ice water and acidified to pH 2 with 2N HCl. The precipitate is filtered and washed with water until neutral, then dried in vacuo to give 9-methoxy-1-methyl-4,5dihydro-1H,3bH-1-benzopyrano[4,5,6-e,f]cyclopentapyrazole-3-carboxylic acid, m.p. 267°-270° C. (3.8 g), which is reacted with thionyl chloride (2.1 ml) in dioxane (150 ml) at the reflux temperature for 1 hour. After cooling the solution is evaporated to dryness in vacuo to yield 9-methoxy-1-methyl-4,5-dihydro-1H,3bH-1-benzopyrano[4,5,6-e,f]cyclopentapyrazole-3-carbonyl chloride (3.9 g). The crude product dissolved in anhydrous dioxane (80 ml) is added under stirring at room temperature to a suspension of the carbanion obtained by treatment of cyanoacetanilide (2.32 g) with 50% sodium hydride (0.76 g) in anhydrous dimethylformamide (15 ml) and anhydrous dioxane (70 ml). The reaction mixture is stirred at room temperature for 45 minutes, then is diluted with ice water and acidified to pH 2 with 2N HCl. The precipitate is filtered, then dissolved in chloroform and the organic solution washed several times with N HCl and then with water until neutral. Evaporation to dryness in vacuo and crystallization from $CH_2Cl_2$/methanol gives 2.7 g of 2-cyano-3-(9-methoxy-1-methyl-4,5-dihydro-1H,3bH-1-benzopyrano[4,5,6-e,f]cyclopentapyrazol-3-yl)-N-phenyl-3-oxo-propanamide, m.p. 262°-264° C., NMR ($CDCl_3$) δ ppm: 1.20-1.90 (m) (1H, C-4 proton), 1.70 (m) (1H, C-4 proton), 3.50-4.80 (m) (3H, C-3b and C-5 protons), 3.91 (s) (3H, —$OCH_3$) 4.36 (s) (3H$>$N—$CH_3$), 6.50-7.70 (m) (7H, phenyl protons), 7.95 (s) (1H, —CONH—), 16.20 (s) (1H, —OH enol).

By proceeding analogously the following compounds can be prepared:

2-cyano-3-(1-methyl-4,5-dihydro-1H,3bH-1-benzopyrano[4,5,6-e,f]cyclopentapyrazol-3-yl)-N-phenyl-3-oxo-propanamide;

2-cyano-3-(9-chloro-1-methyl-4,5-dihydro-1H,3bH-1-benzopyrano[4,5,6-e,f]cyclopentapyrazol-3-yl)-N-phenyl-3-oxo-propanamide, m.p. 244°-246° C.;

2-cyano-3-(1,9-dimethyl-4,5-dihydro-1H,3bH-1-benzopyrano[4,5,6-e,f]cyclopentapyrazol-3-yl)-N-phenyl-3-oxo-propanamide;

2-cyano-3-(7-methoxy-1-methyl-4,5-dihydro-1H,3bH-1-benzopyrano[4,5,6-e,f]cyclopentapyrazol-3-yl)-N-phenyl-3-oxo-propanamide;

2-cyano-3-(9-methoxy-1,5-dimethyl-4,5-dihydro-1H,3bH-1-benzopyrano[4,5,6-e,f]cyclopentapyrazol-3-yl)-N-phenyl-3-oxo-propanamide;

2-cyano-3-(9-fluoro-1-methyl-4,5-dihydro-1H,3bH-1-benzopyrano[4,5,6-e,f]cyclopentapyrazol-3-yl)-N-phenyl-3-oxo-propanamide; and 2-cyano-3-(7-ethoxy-1-methyl-4,5-dihydro-1H,3bH-1-benzopyrano[4,5,6-e,f]cyclopentapyrazol-3-yl)-N-phenyl-3-oxo-propanamide.

EXAMPLE 22

By proceeding according to Example 21, starting from suitable 3-ethoxycarbonyl-4,5-dihydro-1H,3bH-1-benzothiopyrano[4,5,6-e,f]cyclopentapyrazole derivatives, the following compounds can be prepared:

2-cyano-3-(9-methoxy-1-methyl-4,5-dihydro-1H,3bH-1-benzothiopyrano[4,5,6-e,f]cyclopentapyrazol-3-yl)-N-phenyl-3-oxo-propanamide, m.p. 270°-273° C. dec.;

2-cyano-3-(1-methyl-4,5-dihydro-1H,3bH-1-benzothiopyrano[4,5,6e,f]cyclopentapyrazol-3-yl)-N-phenyl-3-propanamide;

2-cyano-3-(9-fluoro-1-methyl-4,5-dihydro-1H,3bH-1-benzothiopyrano[4,5,6-e,f]cyclopentapyrazol-3-yl)-N-phenyl-3-oxo-propanamide;

2-cyano-3-(1,9-dimethyl-4,5-dihydro-1H,3bH-1-benzothiopyrano [4,5,6-e,f]cyclopentapyrazol-3-yl)-N-phenyl-3-oxo-propanamide;

2-cyano-3-(9-methoxy-1-methyl-4,5-dihydro-1H,3bH-1-benzothiopyrano[4,5,6-e,f]cyclopentapyrazol-3-yl-6,6-dioxide)-N-phenyl-3-oxo-propanamide;

2-cyano-3-(7-methoxy-1-methyl-4,5-dihydro-1H,3bH-1-benzothiopyrano[4,5,6-e,f]cyclopentapyrazol-3-yl)-N-phenyl-3-oxo-propanamide; and 2-cyano-3-(1,7-dimethyl-4,5-dihydro-1H,3bH-1-benzothiopyrano[4,5,6-e,f]cyclopentapyrazol-3-yl)-N-phenyl-3-oxo-propanamide.

EXAMPLE 23

Ethyl cyanoacetate (1.4 g) is treated with 50% sodium hydride (0.58 g) in anhydrous dimethylformamide (10 ml) under stirring, at room temperature, until the effervescence subsides. To this solution 9-methoxy-1-methyl-4,5-dihydro-1H,3bH-1-benzopyrano[4,5,6-e,f]cyclopentapyrazole-3-carbonyl chloride (3.04 g), prepared according to Example 21, dissolved in anhydrous dimethylformamide (10 ml) is added under stirring at room temperature. The reaction mixture is allowed to react for 4 hours, then is diluted with ice water and acidified to pH 2 with 37% HCl. The precipitate is extracted with chloroform and the organic solution is washed several times with N HCl and then with water until neutral. After evaporation to dryness in vacuo, the residue is purified over a $SiO_2$ column, using hexane-ethyl acetate as eluent, to give 2-cyano-3-(9-methoxy-1-methyl-4,5-dihydro-1H,3bH-1-benzopyrano[4,5,6-e,f]cyclopentapyrazol-3-oxo-propanoic acid, ethyl ester (1.9 g), which is reacted with aniline (1.5 g) in xylene (100 ml) at the reflux temperature for 48 hours. After cooling the precipitate is filtered and washed with xylene, then crystallized from $CH_2Cl_2$/methanol to give 0.9 g of 2-cyano-3-(9-methoxy-1-methyl-4,5-dihydro-1H,3bH-1-benzopyrano[4,5,6e,f]cyclopentapyrazol-3-yl)-N-phenyl-3-oxo-propanamide, m.p. 262°-264° C.

By proceeding analogously the following compound can be prepared:

2-cyano-3-(9-methoxy-1-methyl-4,5-dihydro-1H,3bH-1-benzothiopyrano[4,5,6-e,f]cyclopentapyrazol-3-yl)-N-phenyl-3-oxo-propanamide.

EXAMPLE 24

By proceeding according to Examples 21 and 22 using suitable cyanoacetanilides, the following compounds can be prepared:

2-cyano-N-cyclohexyl-3-(9-methoxy-1-methyl-4,5-dihydro-1H,3bH-1-benzopyrano[4,5,6-e,f]cyclopentapyrazol-3-yl)-3-oxo-propanamide;

N-(4-chloro-phenyl)-2-cyano-3-(9-methoxy-1-methyl-4,5-dihydro-1H,3bH-1-benzopyrano[4,5,6-e,f]cyclopentapyrazol-3-yl)-3-oxo-propanamide;

N-(3-chloro-phenyl)-2-cyano-3-(9-methoxy-1-methyl-4,5-dihydro-1H,3bH-1-benzopyrano[4,5,6-e,f]cyclopentapyrazol-3-yl)-3-oxo-propanamide;

2-cyano-N-(4-fluoro-phenyl)-3-(9-methoxy-1-methyl-4,5-dihydro-1H,3bH-1-benzopyrano[4,5,6-e,f]cyclopentapyrazol-3-yl)-3-oxo-propanamide;

2-cyano-N-(4-methoxy-phenyl)-3-(9-methoxy-1-methyl-4,5-dihydro-1H,3bH-1-benzopyrano[4,5,6-e,f]cyclopentapyrazol-3-yl)-3-oxo-propanamide;

N-benzyl-2-cyano-3-(9-fluoro-1-methyl-4,5-dihydro-1H,3bH-1-benzopyrano[4,5,6-e,f]cyclopentapyrazol-3-yl)-3-oxo-propanamide;

N-benzyl-2-cyano-3-(9-methoxy-1-methyl-4,5-dihydro-1H,3bH-1-benzothiopyrano[4,5,6-e,f]cyclopentapyrazol-3-yl)-3-oxo-propanamide;

N-benzyl-2-cyano-3-(7-ethoxy-1-methyl-4,5-dihydro-1H,3bH-1-benzopyrano[4,5,6-e,f]cyclopentapyrazol-3-oxo-propanamide;

2-cyano-3-(9-methoxy-1-methyl-4,5-dihydro-1H,3bH-1-benzopyrano[4,5,6-e,f]cyclopentapyrazol-3-yl)-N-(4-methylphenyl)-3-oxo-propanamide;

2-cyano-3-(9-methoxy-1-methyl-4,5-dihydro-1H,3bH-1-benzopyrano[4,5,6-e,f]cyclopentapyrazol-3-yl)-N-(2,6-dimethylphenyl)-3-oxo-propanamide;

2-cyano-3-(9-methoxy-1-methyl-4,5-dihydro-1H,3bH-1-benzopyrano[4,5,6-e,f]cyclopentapyrazol-3-yl)-N-methyl-N-phenyl-3-oxo-propanamide;

N-benzyl-2-cyano-3-(9-methoxy-1-methyl-4,5dihydro-1H,3bH-1-benzopyrano[4,5,6-e,f]cyclopentapyrazol-3-oxo-propanamide;

N-(2-chloro-phenyl)-2-cyano-3-(9-methoxy-1-methyl-4,5-dihydro-1H,3bH-1-benzopyrano[4,5,6-e,f]cyclopentapyrazol-3-yl)-3-oxo-propanamide;

2-cyano-3-(9-methoxy-1-methyl-4,5-dihydro-1H,3bH-1-benzopyrano[4,5,6-e,f]cyclopentapyrazol-3-yl)-N-(3-trifluoromethyl-phenyl)-3-oxo-propanamide;

2-cyano-N-(4-fluoro-phenyl)-3-(7-methoxy-1-methyl-4,5-dihydro-1H,3bH-1-benzopyrano[4,5,6-e,f]cyclopentapyrazol-3-yl)-3-oxo-propanamide;

2-cyano-N-(4-fluoro-phenyl)-3-(9-fluoro-1-methyl-4,5-dihydro-1H,3bH-1-benzopyrano[4,5,6-e,f]cyclopentapyrazol-3-yl)-3-oxo-propanamide;

2-cyano-3-(9-fluoro-1-methyl-4,5-dihydro-1H,3bH-1-benzothiopyrano[4,5,6-e,f]cyclopentapyrazol-3-yl)-N-(3-chlorophenyl)-3-oxo-propanamide;

2-cyano-N-(3-fluoro-phenyl)-3-(9-methoxy-1-methyl-4,5-dihydro-1H,3bH-1-benzopyrano[4,5,6-e,f]cyclopentapyrazol-3-yl)-3-oxo-propanamide;

2-cyano-3-(9-methoxy-1-methyl-4,5-dihydro-1H,3bH-1-benzopyrano[4,5,6-e,f]cyclopentapyrazol-3-yl)-N-(3-methylphenyl)-3-oxo-propanamide;

2-cyano-3-(9-methoxy-1-methyl-4,5-dihydro-1H,3bH-1-benzopyrano[4,5,6-e,f]cyclopentapyrazol-3-yl)-N-(3-methoxyphenyl)-3-oxo-propanamide;

N-(3-chloro-phenyl)-2-cyano-3-(9-methoxy-1-methyl-4,5-dihydro-1H,3bH-1-benzothiopyrano]4,5,6-e,f]cyclopentapyrazol-3-yl)-3-oxo-propanamide;

2-cyano-N-(3-fluoro-phenyl)-3-(9-methoxy-1-methyl-4,5-dihydro-1H,3bH-1-benzothiopyrano[4,5,6-e,f]cyclopentapyrazol-3-yl)-3-oxo-propanamide;

N-benzyl-2-cyano-3-(7-chloro-1-methyl-4,5-dihydro-1H,3bH-1-benzopyrano[4,5,6-e,f]cyclopentapyrazol-3-yl)-3-oxo-propanamide;

N-benzyl-2-cyano-3-(1-methyl-4,5-dihydro-1H,3bH-1-benzothiopyrano[4,5,6-e,f]cyclopentapyrazol-3-yl)-3-oxo-propanamide;

N-benzyl-2-cyano-3-(7-methoxy-1-methyl-4,5-dihydro-1H,3bH-1-benzopyrano[4,5,6-e,f]cyclopentapyrazol-3-yl)-3-oxo-propanamide;

N-benzyl-2-cyano-3-(7-methoxy-1-methyl-4,5-dihydro-1H,3bH-1-benzothiopyrano[4,5,6-e,f]cyclopentapyrazol-3-yl)-3-oxo-propanamide;

N-benzyl-2-cyano-3-(9-methoxy-1,5-dimethyl-4,5-dihydro-1H,3bH-1-benzopyrano[4,5,6-e,f]cyclopentapyrazol-3-yl)-3-oxo-propanamide;

N-(3,5-dichloro-phenyl)-2-cyano-3-(9-methoxy-1-methyl-4,5-dihydro-1H,3bH-1-benzopyrano[4,5,6-e,f]cyclopentapyrazol-3-yl)-3-oxo-propanamide;

N-(3-chloro-phenyl)-2-cyano-3-(7-methoxy-1-methyl-4,5-dihydro-1H,3bH-1-benzopyrano[4,5,6-e,f]cyclopentapyrazol-3-yl)-3-oxo-propanamide;

2-cyano-N-(3-fluoro-phenyl)-3-(7-methoxy-1-methyl-4,5-dihydro-1H,3bH-1-benzopyrano[4,5,6-e,f]cyclopentapyrazol-3-yl)-3-oxo-propanamide;

N-(3-chloro-phenyl)-2-cyano-3-(9-fluoro-1-methyl-4,5-dihydro-1H,3bH-1-benzopyrano[4,5,6-e,f]cyclopentapyrazol-3-yl)-3-oxo-propanamide;

2-cyano-N-(4-fluoro-phenyl)-3-(9-fluoro-1-methyl-4,5-dihydro-1H,3bH-1-benzopyrano[4,5,6-e,f]cyclopentapyrazol-3-yl)-3-oxo-propanamide;

2-cyano-N-(3-fluoro-phenyl)-3-(9-fluoro-1-methyl-4,5-dihydro-1H,3bH-1-benzopyrano[4,5,6-e,f]cyclopentapyrazol-3-yl)-3-oxo-propanamide;

2-cyano-N-(4-fluoro-phenyl)-3-(9-methoxy-1,5-dimethyl-4,5-dihydro-1H,3bH-1-benzopyrano[4,5,6-e,f]cyclopentapyrazol-3-yl)-3-oxo-propanamide;
2-cyano-N-(3-fluoro-phenyl)-3-(9-methoxy-1,5-dimethyl-4,5-dihydro-1H,3bH-1-benzopyrano[4,5,6-e,f]cyclopentapyrazol-3-yl)-3-oxo-propanamide;
N-(3-chloro-phenyl)-2-cyano-3-(9-methoxy-1,5-dimethyl-4,5-dihydro-1H,3bH-1-benzopyrano[4,5,6-e,f]cyclopentapyrazol-3-yl)-3-oxo-propanamide;
2-cyano-N-(4-fluoro-phenyl)-3-(1-methyl-4,5-dihydro-1H,3bH-1-benzothiopyrano[4,5,6-e,f]cyclopentapyrazol-3-yl)-3-oxo-propanamide;
2-cyano-3-(1-methyl-4,5-dihydro-1H,3bH-1-benzothiopyrano[4,5,6-e,f]cyclopentapyrazol-3-yl)-N-(3-chloro-phenyl)-3-oxo-propanamide;
2-cyano-N-(4-fluoro-phenyl)-3-(9-chloro-1-methyl-4,5-dihydro-1H,3bH-1-benzothiopyrano[4,5,6-e,f]cyclopentapyrazol-3-yl)-3-oxo-propanamide;
2-cyano-N-(4-fluoro-phenyl)-3-(9-methoxy-1-methyl-4,5-dihydro-1H,3bH-1-benzothiopyrano[4,5,6-e,f]cyclopentapyrazol-3)-3-oxo-propanamide; and
2-cyano-3-(9-chloro-1-methyl-4,5-dihydro-1H,3bH-1-benzopyrano[4,5,6-e,f]cyclopentapyrazol-3-yl)-N-(3-chloro-phenyl)-3-oxo-propanamide.

EXAMPLE 25

9-chloro-1-methyl-3-methylsulfinylacetyl-4,5-dihydro-1H,3bH-1-benzopyrano[4,5,6-e,f]cyclopentapyrazole is dissolved by treatment with an equivalent amount of sodium ethoxide in ethanol. The solution is evaporated to dryness and the residue is treated with isopropyl ether and then filtered to give the sodium salt of 9-chloro-1-methyl-3-methylsulfinylacetyl-4,5-dihydro-1H,3bH-1-benzopyrano[4,5,6-e,f]cyclopentapyrazole, m.p. >300° C.

By proceeding analogously the sodium salts of the following compounds can be prepared:

9-methoxy-1-methyl-3-methylsulfinylacetyl-4,5-dihydro-1H,3bH-1-benzothiopyrano[4,5,6-e,f]cyclopentapyrazole;
1-methyl-3-methylsulfinylacetyl-4,5-dihydro-1H,3bH-1-benzothiopyrano[4,5,6-e,f]cyclopentapyrazole; and
9-fluoro-1-methyl-3-methylsulfinylacetyl-4,5-dihydro-1H,3bH-1-benzothiopyrano[4,5,6-e,f]cyclopentapyrazole.

EXAMPLE 26

2-Cyano-3-(9-chloro-1-methyl-4,5-dihydro-1H,3bH-1-benzopyrano[4,5,6-e,f]cyclopentapyrazol-3-yl)-N-phenyl-3-oxo-propanamide is dissolved by treatment with an equivalent amount of sodium ethoxide in ethanol. The solution is evaporated to dryness and the residue is treated with isopropyl ether and then filtered to give the sodium salt of 2-cyano-3-(9-chloro-1-methyl-4,5-dihydro-1H,3bH-1-benzopyrano[4,5,6-e,f]cyclopentapyrazol-3-yl)-N-phenyl-3-oxo-propanamide, m.p. >300° C.

By proceeding analogously the sodium salts of the following compounds can be prepared:

2-cyano-3-(9-methoxy-1-methyl-4,5-dihydro-1H,3bH-1-benzopyrano[4,5,6-e,f]cyclopentapyrazol-3-yl)-N-phenyl-3-oxo-propanamide;
2-cyano-3-(9-methoxy-1-methyl-4,5-dihydro-1H,3bH-1-benzothiopyrano[4,5,6-e,f]cyclopentapyrazol-3-yl)-N-phenyl-3-oxo-propanamide; and
2-cyano-3-(1-methyl-4,5-dihydro-1H,3bH-1-benzothiopyrano[4,5,6-e,f]cyclopentapyrazol-3-yl)-N-phenyl-3-oxo-propanamide.

EXAMPLE 27

Tablets, each weighing 150 mg and containing 50 mg of active substance, can be manufactured as follows:

| Composition (for 10000 tablets) | |
|---|---|
| 1-methyl-3-methylsulfinylacetyl-3b,4,5,6-tetrahydro-1H—acenaphthyleno[1,2-c]pyrazole | 500 g |
| Lactose | 710 g |
| Corn starch | 238 g |
| Talc powder | 36 g |
| Magnesium stearate | 16 g |

1-Methyl-3-methylsulfinylacetyl-3b,4,5,6-tetrahydro-1H-ascenaphthyleno[1,2-c]pyrazole, lactose and a half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size of 1.4 mm, then the remaining quantity of starch, talc and magnesium stearate is added, carefully mixed and processed into tablets using punches of 8 mm diameter.

EXAMPLE 28

Tablets, each weighing 150 mg and containing 50 mg of active substance, can be manufactured as follows:

| Composition (for 10000 tablets) | |
|---|---|
| 2-cyano-3-(1-methyl-3b,4,5,6-tetrahydro-1H—acenaphthyleno[1,2-c]pyrazol-3-yl)-N—phenyl-3-oxo-propanamide | 500 g |
| Lactose | 710 g |
| Corn starch | 238 g |
| Talc powder | 36 g |
| Magnesium stearate | 16 g |

2-Cyano-3-(1-methyl-3b,4,5,6-tetrahydro-1H-acenaphthyleno[1,2-c]pyrazol-3-yl)-N-phenyl-3-oxo-propanamide, lactose and half of the corn starch are mixed; the mixture is then forced through a sieve of 0,5 mm openings. Corn starch (18 g) is suspended in warm water (180 ml). The resulting paste is used to granulate the powder. The granules are dried, comminuted on a sieve of sieve size 1.4 mm, then remaining quantity of starch, talc and magnesium stearate is added, carefully mixed and processed into tablets using punches of 8 mm diameter.

EXAMPLE 29

By proceeding according to Examples 27 and 28, tablets can be prepared having the same composition, but containing, for example, as active substance, one of the following compounds:

9-fluoro-1-methyl-3-methylsulfinylacetyl-4,5-dihydro-1H,3bH-1-benzopyrano[4,5,6-e,f]cyclopentapyrazole;
2-cyano-3-(9-methoxy-1-methyl-4,5-dihydro-1H,3bH-1-benzopyrano[4,5,6-e,f]cyclopentapyrazole-3-yl)-N-phenyl-3-oxo-propanamide;
2-cyano-3-(9-methoxy-1-methyl-4,5-dihydro-1H,3bH-1-benzothiopyrano[4,5,6-e,f]cyclopentapyrazol-3-yl)-N-phenyl-3-oxo-propanamide;
N-benzyl-2-cyano-3-9-methoxy-1-methyl-4,5-dihydro-1H,3bH-1-benzopyrano[4,5,6-e,f]cyclopentapyrazol-3-yl)-3-oxo-propanamide;

2-cyano-3-9-fluoro-1-methyl-4,5-dihydro-1H,3bH-1-benzopyrano[4,5,6-e,f]cyclopentapyrazol-3-yl)-N-phenyl-3-oxo-propanamide; and N-benzyl-2-cyano-(9-fluoro-1-methyl-4,5-dihydro-1H,3bH-1-benzopyrano[4,5,6-e,f]cyclopentapyrazol-3-yl)-3-oxo-propanamide.

We claim:

1. A compound having the following general formula (I)

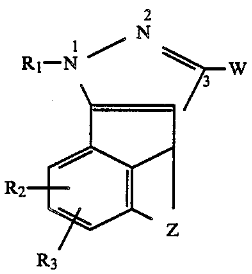

wherein

Z represents a $C_2$–$C_6$ alkylene chain or a —CH=CH—CH= group or an —E—$CHR_4$—$(CH_2)_p$— group, in which p is zero, 1 or 2;

E represents an oxygen atom or a $>S(O)_q$ group, wherein q is zero, 1 or 2; and $R_4$ is hydrogen or $C_1$–$C_3$ alkyl;

$R_1$ represents $C_1$–$C_6$ alkyl, benzyl, pyridyl or phenyl, the phenyl being unsubstituted or substituted by one or two substituents chosen independently from halogen, trifluoromethyl, $C_1$–$C_6$ alkyl, $C_1$–$C_6$ alkoxy, nitro, amino, formylamino and $C_2$–$C_8$ alkanoylamino;

each of $R_2$ and $R_3$ is independently:

(a) hydrogen, halogen or $C_1$–$C_6$ alkyl;

(b) hydroxy, $C_1$–$C_6$ alkoxy or $C_3$–$C_4$ alkenyloxy; or (c) nitro, amino, formylamino or $C_2$–$C_8$ alkanoylamino; and W represents:

(a') a

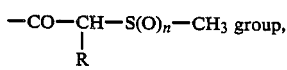

wherein n is 1 or 2 and R represents hydrogen or $C_1$–$C_6$ alkyl; or (b') a

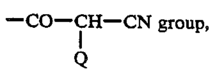

wherein Q represents hydrogen, carboxy, $CONH_2$, $C_2$–$C_7$ alkoxycarbonyl or a

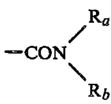

or a

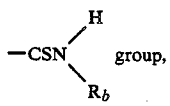

wherein $R_a$ represents hydrogen or $C_1$–$C_{20}$ alkyl and $R_b$ represents $C_1$–$C_{20}$ alkyl or a —$(CH_2)_m$—$R_5$ group, wherein m is zero, 1 or 2 and $R_5$ is:

(a") $C_5$–$C_8$ cycloalkyl;

(b") pyridyl unsubstituted or substituted by one or two substituents chosen independently from halogen, $C_1$–$C_6$ alkyl and $C_1$–$C_6$ alkoxy; or (c") phenyl unsubstituted or substituted by one or two substituents independently chosen from halogen, $CF_3$, $C_1$–$C_6$ alkyl, $C_1$–$C_6$ alkoxy, amino, nitro, formylamino, $C_2$–$C_8$ alkanoylamino, di($C_1$–$C_6$ alkyl)amino, hydroxy, formyloxy and $C_2$–$C_8$ alkanoyloxy, and the pharmaceutically acceptable salts thereof.

2. A compound of formula (I) according to claim 1, wherein

Z represents a $C_2$–$C_4$ alkylene chain or a —CH=CH—CH= group or an —E—$CHR_4$—$(CH_2)_p$— group, in which p is zero, 1 or 2; E represents an oxygen atom or a $>S(O)_q$ group, wherein q is zero, 1 or 2; and $R_4$ is hydrogen or $C_1$–$C_3$ alkyl;

$R_1$ represents $C_1$–$C_4$ alkyl or phenyl, the phenyl being unsubstituted or substituted by one or two substituents chosen independently from amino, halogen, trifluoromethyl, $C_1$–$C_4$ alkyl, $C_1$–$C_4$ alkoxy and nitro;

each of $R_2$ and $R_3$ is independently hydrogen, halogen, $C_1$–$C_4$ alkyl or $C_1$–$C_4$ alkoxy;

W represents:

a

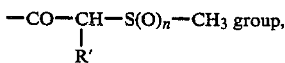

wherein n is 1 or 2 and R' represents hydrogen or $C_1$–$C_4$ alkyl; or a

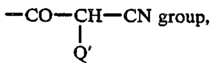

wherein Q' represents hydrogen, —$CONH_2$, $C_2$–$C_5$ alkoxycarbonyl or a —$CONR'_aR'_b$ or —$CSNHR'_b$ group, wherein $R'_a$ is hydrogen or $C_1$–$C_6$ alkyl and $R'_b$ is $C_1$–$C_6$ alkyl or a —$(CH_2)_{m'}$—$R'_5$ group wherein m' is 0 or 1 and $R'_5$ is $C_5$–$C_8$ cycloalkyl, unsubstituted pyridyl or phenyl unsubstituted or substituted by one or two substituents chosen independently from halogen, $CF_3$, $C_1$–$C_4$ alkyl, $C_1$–$C_4$ alkoxy, nitro and amino; and the pharmaceutically acceptable salts thereof.

3. A compound of formula (I) according to claim 1, wherein

Z represents a $C_3$–$C_4$ alkylene chain or a —CH=CH—CH= group or an E'—$CHR'_4$—$CH_2$— group, in which E' represents an oxygen or a sulphur atom and $R'_4$ is hydrogen or $C_1$–$C_3$ alkyl;

$R_1$ represents $C_1$–$C_2$ alkyl or phenyl, the phenyl being unsubstituted or substituted by halogen, trifluoromethyl, $C_1$–$C_4$ alkyl or $C_1$–$C_4$ alkoxy;

$R_2$ is hydrogen;

$R_3$ represents hydrogen, halogen, $C_1$–$C_4$ alkyl or $C_1$–$C_4$ alkoxy;

W represents:

a

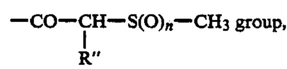

wherein n is 1 or 2 and

R'' represents hydrogen or methyl; or a

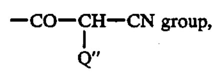

wherein Q'' represents hydrogen, $C_2$–$C_3$ alkoxycarbonyl or a —CONR''$_a$R''$_b$ or —CSNHR''$_b$ group wherein R''$_a$ is hydrogen or methyl and R''$_b$ is $C_1$–$C_6$ alkyl or a —$(CH_2)_{m'}$—R''$_5$ group in which m' is zero or 1 and R''$_5$ is $C_5$–$C_6$ cycloalkyl or it is phenyl unsubstituted or substituted by one or two substituents chosen independently from halogen, $CF_3$, nitro, amino, methyl and methoxy; and the pharmaceutically acceptable salts thereof.

4. A compound selected from the group consisting of:

1-methyl-3-methylsulfinylacetyl-3b,4,5,6-tetrahydro-1H-acenaphthyleno[1,2-c]pyrazole;

1,9-dimethyl-3-methylsulfinylacetyl-1H-acenaphthyleno[1,2-c]pyrazole;

1,6-dimethyl-3-methylsulphinylacetyl-3b,4,5,6-tetrahydro-1H-acenaphthyleno[1,2-c]pyrazole;

2-cyano-3-(1-methyl-1H-acenaphthyleno[1,2-c]pyrazol-3-yl)-N-phenyl-3-oxo-propanamide;

N-benzyl-2-cyano-3-(1-methyl-1H-acenaphthyleno[1,2-c]pyrazol-3-yl)-3-oxo-propanamide;

2-cyano-N-(4-fluoro-phenyl)-3-(1-methyl-3b,4,5,6-tetrahydro-1H-acenaphthyleno[1,2-c]pyrazol-3-yl)-3-oxo-propanamide;

N-benzyl-2-cyano-3-(1-methyl-3b,4,5,6-tetrahydro-1H-acenaphthyleno[1,2-c]pyrazol-3-yl)-3-oxo-propanamide;

2-cyano-3-(9-methoxy-1-methyl-4,5-dihydro-1H,3bH-1-benzopyrano[4,5,6-e,f]cyclopentapyrazol-3-yl)-N-phenyl-3-oxo-propanamide;

9-fluoro-1-methyl-3-methylsulfinylacetyl-4,5-dihydro-1H,3bH-1-benzopyrano[4,5,6-e,f]cyclopentapyrazole;

N-benzyl-2-cyano-3-(9-methoxy-1-methyl-4,5-dihydro-1H,3bH-1-benzopyrano[4,5,6-e,f]cyclopentapyrazol-3-yl)-3-oxo-propanamide;

2-cyano-N-(4-fluoro-phenyl)-3-(9-methoxy-1-methyl-4,5-dihydro-1H,3bH-1-benzopyrano[4,5,6-e,f]cyclopentapyrazol-3-yl)-3-oxo-propanamide;

2-cyano-N-(3-fluoro-phenyl)-3-(9-methoxy-1-methyl-4,5-dihydro-1H,3bH-1-benzopyrano[4,5,6-e,f]cyclopentayrazol-3-yl)-3-oxo-propanamide;

N-(3-chloro-phenyl)-2-cyano-3-(9-methoxy-1-methyl-4,5-dihydro-1H,3bH-1-benzopyrano[4,5,6-e,f]cyclopentapyrazol-3-yl)-3-oxo-propanamide;

N-benzyl-2-cyano-3-(9-methoxy-1,5-dimethyl-4,5-dihydro-1H,3bH-1-benzopyrano[4,5,6-e,f]cyclopentapyrazol-3-yl)-3-oxo-propanamide;

2-cyano-3-(9-methoxy-1,5-dimethyl-4,5-dihydro-1H,3bH-1benzopyrano[4,5,6-e,f]cyclopentapyrazol-3-yl)-N-phenyl-3-oxo-propanamide;

N-benzyl-2-cyano-3-(9-methoxy-1-methyl-4,5-dihydro-1H,3bH-1-benzothiopyrano[4,5,6-e,f]cyclopentapyrazol-3-yl)-3-oxo-propanamide;

2-cyano-3-(9-methoxy-1-methyl-4,5-dihydro-1H,3bH-1benzothiopyrano[4,5,6-e,f]cyclopentapyrazol-3-yl)-N-phenyl-3-oxo-propanamide;

2-cyano-N-(4-fluoro-phenyl)-3-(9-methoxy-1-methyl-4,5-dihydro-1H,3bH-1-benzothiopyrano[4,5,6-e,f]cyclopentapyrazol-3-yl)-3-oxo-propanamide;

N-benzyl-2-cyano-3-(9-methoxy-1-methyl-3b,4,5,6-tetrahydro-1H-acenaphthyleno[1,2c]pyrazol-3-yl)-3-oxo-propanamide;

2-cyano-3-(9-methoxy-1-methyl-3b,4,5,6-tetrahydro-1H-acenaphthyleno[1,2-c]pyrazol-3-yl)-N-phenyl-3-oxo-propanamide;

2-cyano-N-(4-fluoro-phenyl)-3-(9-methoxy-1-methyl-3b,4,5,6-tetrahydro-1H-acenaphthyleno[1,2-c]pyrazol-3-yl)-3-oxo-propanamide;

2-cyano-3-(9-fluoro-1-methyl-4,5-dihydro-1H,3bH-1-benzopyrano[4,5,6-e,f]cyclopentapyrazol-3-yl)-N-phenyl-3-oxo-propanamide;

N-benzyl-2-cyano-3-(9-fluoro-1-methyl-4,5-dihydro-1H,3bH-1-benzopyrano[4,5,6-e,f]cyclopentapyrazol-3-yl)-3-oxo-propanamide;

2-cyano-N-(4-fluoro-phenyl)-3-(9-fluoro-1-methyl-4,5-dihydro-1H,3bH-1-benzopyrano[4,5,6-e,f]cyclopentapyrazol-3-yl)-3-oxo-propanamide;

and the pharmaceutically acceptable salts thereof.

5. A pharmaceutically acceptable salt of a compound of claim 4, wherein the salt is the sodium or potassium salt.

6. A pharmaceutical composition suitable for treating bacterial and viral infections in mammals, comprising, as an immunomodulating agent, a compound of formula (I) according to claim 1, or a pharmaceutically acceptable salt thereof, in association with a suitable carrier and/or diluent, said compound or salt being in an amount effective to cause immunomodulating activity thereby treating a bacterial or a viral infection in a mammal.

7. A method of treating bacterial and viral infections in a mammal in need of such treatment, said method comprising administering to said mammal a compound of formula (I) according to claim 1, or a pharmaceutically acceptable salt thereof, said compound or salt being in an amount effective to cause immunomodulating activity thereby treating a bacterial or a viral infection in a mammal.

* * * * *